United States Patent
Shin et al.

(10) Patent No.: US 8,999,530 B2
(45) Date of Patent: Apr. 7, 2015

(54) COMPOUNDS AND ORGANIC ELECTRONIC DEVICE USING SAME

(75) Inventors: Changhwan Shin, Daejeon (KR); Kongkyeom Kim, Daejeon (KR); Dong Hoon Lee, Daejeon (KR); Jungi Jang, Daejeon (KR); Minseung Chun, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/125,552

(22) PCT Filed: Jun. 12, 2012

(86) PCT No.: PCT/KR2012/004629
§ 371 (c)(1),
(2), (4) Date: Dec. 11, 2013

(87) PCT Pub. No.: WO2012/173371
PCT Pub. Date: Dec. 20, 2012

(65) Prior Publication Data
US 2014/0138659 A1  May 22, 2014

(30) Foreign Application Priority Data
Jun. 13, 2011  (KR) .......... 10-2011-0056777

(51) Int. Cl.
*H01L 51/00* (2006.01)
*C09K 11/06* (2006.01)
*H05B 33/10* (2006.01)
(Continued)

(52) U.S. Cl.
CPC ........ *H01L 51/0052* (2013.01); *H01L 51/0072* (2013.01); *C09K 11/06* (2013.01); *H05B 33/10* (2013.01); *H01L 51/0058* (2013.01); *C07D 487/04* (2013.01); *H01L 51/5072* (2013.01); *Y02E 10/549* (2013.01); *C09K 2211/1007* (2013.01); *C09K 2211/1011* (2013.01); *C09K 2211/1014* (2013.01); *C09K 2211/1044* (2013.01); *H01L 51/006* (2013.01); *H01L 51/0068* (2013.01); *H01L 51/0077* (2013.01);
(Continued)

(58) Field of Classification Search
None
See application file for complete search history.

(56) References Cited

U.S. PATENT DOCUMENTS

2005/0123795 A1  6/2005  Lussier et al.
2006/0269784 A1  11/2006  Leipold et al.
(Continued)

FOREIGN PATENT DOCUMENTS

CN  101291935 A  10/2008
CN  101415718 A  4/2009
(Continued)

OTHER PUBLICATIONS
"Multifunctional Deep-Blue Emitter Comprising an Anthracene Cor and Terminal Triphenylphosphine Oxide Groups";' Chien, et al; Adv. Funct. Mater. 2009, 19, 560-566.

*Primary Examiner* — Gregory Clark
(74) *Attorney, Agent, or Firm* — McKenna Long & Aldridge LLP

(57) ABSTRACT

The present invention provides a new compound and an organic electronic device using the same. The compound according to the present invention may serve as hole injection, hole transporting, electron injection and transporting, and light emitting materials and the like in an organic electronic device comprising an organic light emitting device, and the organic electronic device according to the present invention shows excellent properties in terms of efficiency, driving voltage and service life.

8 Claims, 2 Drawing Sheets

(51) Int. Cl.
  *C07D 487/04* (2006.01)
  *H01L 51/50* (2006.01)

(52) U.S. Cl.
  CPC .......... *H01L 51/0081* (2013.01); *Y10S 428/917* (2013.01)

(56) References Cited

U.S. PATENT DOCUMENTS

| | | | |
|---|---|---|---|
| 2007/0131929 A1* | 6/2007 | Bae et al. | 257/40 |
| 2011/0127513 A1 | 6/2011 | Lee et al. | |
| 2011/0284799 A1 | 11/2011 | Stoessel et al. | |
| 2011/0303901 A1* | 12/2011 | Cheng et al. | 257/40 |
| 2012/0261651 A1 | 10/2012 | Noto et al. | |

FOREIGN PATENT DOCUMENTS

| | | |
|---|---|---|
| JP | 2004-095221 | 3/2004 |
| JP | 2004095221 A | 3/2004 |
| JP | 2007-109988 | 4/2007 |
| JP | 2010-278376 | 12/2010 |
| JP | 2010278376 A | 12/2010 |
| KR | 10-2005-0037337 | 4/2005 |
| KR | 10-2005-0037337 A | 4/2005 |
| KR | 20050037337 A | 4/2005 |
| KR | 20060109524 A | 10/2006 |
| KR | 10-2007-0095042 | 9/2007 |
| WO | 2007-064479 | 6/2007 |
| WO | 2007-069847 | 6/2007 |
| WO | 2007-095118 | 8/2007 |
| WO | 2008120957 A1 | 10/2008 |
| WO | 2009-100991 | 8/2009 |
| WO | 2010-062065 | 6/2010 |
| WO | 2010/086089 A1 | 8/2010 |
| WO | 2011/010842 A2 | 1/2011 |
| WO | 2011-021385 | 2/2011 |
| WO | 2011/021385 A1 | 2/2011 |

* cited by examiner

COMPOUNDS AND ORGANIC ELECTRONIC DEVICE USING SAME

This application is a national stage application of International Application No. PCT/KR2012/004629, filed on Jun. 12, 2012, which claims priority to and the benefit of Korean Patent Application Nos. 10-2011-0056777, filed Jun. 13, 2011, in the Korean Intellectual Property Office, the entire contents of which are incorporated herein by reference.

TECHNICAL FIELD

The present invention relates to a new compound and an organic electronic device using the same.

BACKGROUND ART

In the present specification, an organic electronic device is an electronic device using an organic semiconductor material, and requires exchanging of holes and/or electrons between electrodes and organic semiconductor materials. The organic electronic device may be largely divided into the following two categories according to an operation principle. First, there is an electronic device in which an exiton is formed in an organic material layer by a photon that flows from an external light source to the device, the exiton is separated into electrons and holes, and the electrons and the holes are transferred to the other electrodes, respectively and used as a current source (voltage source). Second, there is an electronic device in which holes and/or electrons are injected into organic semiconductor material layers forming an interface with the electrode by applying a voltage or a current to two or more electrodes, and the device is operated by the injected electrons and holes.

As examples of the organic electronic device, there are an organic light emitting device, an organic solar cell, an organic photoconductor (OPC) drum, an organic transistor and the like, and an electron/hole injection material, an electron/hole extraction material, an electron/hole transporting material or a light emitting material is required in order to drive all these devices. Hereinafter, an organic light emitting device will be mainly described in detail. However, in the organic electronic devices, all of the electron/hole injection material, the electron/hole extraction material, the electron/hole transporting material and the light emitting material are operated based on a similar principle.

In general, an organic light emitting phenomenon refers to a phenomenon that converts electric energy into light energy by using an organic material. The organic light emitting device using the organic light emitting phenomenon has a structure which typically comprises an anode, a cathode, and an organic material layer that is disposed therebetween. Herein, organic material layers frequently have a multilayer structure that comprises different materials in order to enhance efficiency and stability of the organic light emitting device, and for example, and may comprise a hole injection layer, a hole transporting layer, a light emitting layer, an electron transporting layer, an electron injection layer and the like. In the structure of the organic light emitting device, if a voltage is applied between two electrodes, holes are injected from an anode into the organic material layer and electrons are injected from a cathode into the organic material layer, and when the injected holes and the electrons meet each other, an exciton is formed, and light is emitted when the exciton falls to a bottom state. It is known that this organic light emitting device has properties such as self light emission, high brightness, high efficiency, low driving voltage, a wide viewing angle, high contrast, high speed response and the like.

In the organic light emitting device, the material that is used as the organic material layer may be classified into a light emitting material and an electric charge transporting material, for example, a hole injection material, a hole transporting material, an electron transporting material, an electron injection material and the like according to a function thereof. Examples of the light emitting material include blue, green, and red light emitting materials and yellow and orange light emitting materials required for realizing better natural colors according to the emission color. In addition, in order to increase color purity and increase light emission efficiency through energy transfer, a host/dopant system may be used as the light emitting material. In the principle, by mixing a dopant that has an energy bandwidth gap that is lower than that of a host mainly constituting the light emitting layer and has excellent light emission efficiency with a light emitting layer in a small amount, an exciton that is generated in the host is transported to the dopant to produce light having high efficiency. At this time, since the wavelength of the host moves to the wavelength bandwidth of the dopant, light at a desired wavelength may be obtained according to the kind of dopant used.

In order to sufficiently show excellent properties of the above-described organic light emitting device, a material constituting the organic material layer in the device, for example, a hole injection material, a hole transporting material, a light emitting material, an electron transporting material, the electron injection material and the like need to be mainly supported by stable and efficient materials, but the development of a stable and efficient organic material layer material for organic light emitting device has not been sufficiently achieved. Accordingly, there is a continuous need for developing a new material.

DETAILED DESCRIPTION OF THE INVENTION

Technical Problem

The present inventors have found out a compound having a new structure. In addition, the inventors have found out the fact that when an organic material layer of an organic electron device is formed by using the new compound, effects such as an increase in efficiency of the device, a drop in driving voltage, an increase in stability and the like can be obtained.

Thus, an object of the present invention is to provide a new compound and an organic electronic device using the same.

Technical Solution

The present invention provides a compound represented by the following Formula 1.

[Formula 1]

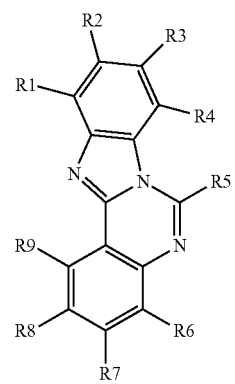

wherein at least one of R1 to R9 is represented by the following Formula 2 and the rest thereof are hydrogen; deuterium; a halogen group; a nitrile group; a nitro group; a hydroxyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heterocyclic group comprising one or more of N, O, and S atoms; and

[Formula 2]

L is a direct bond; a substituted or unsubstituted arylene group; or a substituted or unsubstituted heteroarylene group comprising one or more of N, O and S atoms, Ar1 and Ar2 are each independently a substituted or unsubstituted aryl group; or a substituted or unsubstituted heterocyclic group comprising one or more of N, O and S atoms; and A is O, S or Se.

In addition, the present invention provides an organic electron device comprising a first electrode, a second electrode, and one or more organic material layers disposed between the first electrode and the second electrode, wherein one or more layers of the organic material layers comprise a compound represented by Formula 1.

Advantageous Effects

The new compound according to the present invention may be used as a material for an organic material layer of an organic electronic device comprising an organic light emitting device by introducing various substituent groups and the like. The organic electronic device comprising an organic light emitting device using the compound represented by Formula 1 according to the present invention as a material for an organic material layer shows excellent properties in terms of efficiency, driving voltage, service life and the like.

BEST MODE

Figure 1:
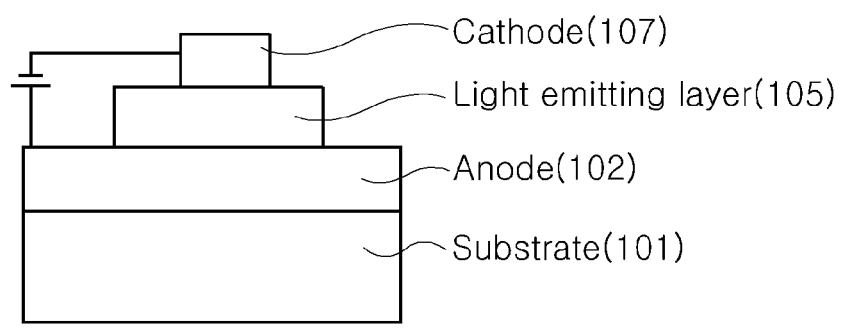
FIG. 1 illustrates a structure of an organic light emitting device in which an anode 102, a light emitting layer 105, and a cathode 107 are sequentially stacked on a substrate 101.

Hereinafter, the present invention will be described in more detail.

A new compound according to the present invention is represented by Formula 1.

In Formula 1, R5 may be represented by Formula 2, but is not limited thereto.

In the compound according to the present invention, the substituent groups in Formula 1 will be described in more detail as follows.

The alkyl group may be straight or branched, and the number of carbon atoms thereof is not particularly limited, but is preferably 1 to 12. Specific examples thereof include a methyl group, an ethyl group, a propyl group, an isopropyl group, a butyl group, a t-butyl group, a pentyl group, a hexyl group, a heptyl group and the like, but are not limited thereto.

The alkenyl group may be straight or branched, and the number of carbon atoms thereof is not particularly limited, but is preferably 2 to 12. Specific examples thereof include an alkenyl group linked with an aryl group such as a stylbenzyl group, a styrenyl group and the like, but are not limited thereto.

The alkynyl group may be straight or branched, and the number of carbon atoms thereof is not particularly limited, but is preferably 2 to 12. Specific examples thereof include an ethynyl group, a propynyl group and the like, but are not limited thereto.

The cycloalkyl group is preferably a group having 3 to 12 carbon atoms, which does not cause a steric hindrance. Specific examples thereof include a cyclopentyl group, a cyclohexyl group and the like, but are not limited thereto.

The cycloalkenyl group preferably has 3 to 12 carbon atoms, and more specific examples thereof include a ring compound having ethenylene in a pentagonal or hexagonal ring, and the like, but are not limited thereto.

The alkoxy group preferably has 1 to 12 carbon atoms, and more specific examples thereof include methoxy, ethoxy, isopropyloxy and the like, but are not limited thereto.

The aryloxy group preferably has 6 to 20 carbon atoms, and more specific examples thereof include phenyloxy, cyclohexyloxy, naphthyloxy, diphenyloxy and the like, but are not limited thereto.

The alkylamine group preferably has 1 to 30 carbon atoms, and more specific examples thereof include a methylamine group, a dimethylamine group, an ethylamine group, a diethylamine group and the like, but are not limited thereto.

The arylamine group preferably has 5 to 30 carbon atoms, and more specific examples thereof include a phenylamine group, a naphthylamine group, a biphenylamine group, an anthracenylamine group, a 3-methyl-phenylamine group, a 4-methyl-naphthylamine group, a 2-methyl-biphenylamine group, a 9-methyl-anthracenylamine group, a diphenylamine group, a phenylnaphthylamine group, a ditolylamine group, a phenyltolylamine group, a triphenylamine group and the like, but are not limited thereto.

The aryl group may be monocyclic or polycyclic, and the number of carbon atoms thereof is not particularly limited, but is preferably 6 to 40. Examples of the monocyclic aryl group include a phenyl group, a biphenyl group, a terphenyl group, stilbene and the like, and examples of the polycyclic aryl group include a naphthyl group, an anthracenyl group, a phenanthrene group, a pyrenyl group, a perylenyl group, a chrysenyl group, a fluorenyl group, and the like, but are not limited thereto.

The heteroaryl group is a ring group comprising O, N, S, or P as a heterogeneous atom, and the number of carbon atoms is not particularly limited, but is preferably 3 to 30. Examples of the heterocyclic group include a carbazole group, a thiophene group, a furan group, a pyrrole group, an imidazole group, a thiazole group, an oxazole group, an oxadiazole group, a triazole group, a pyridyl group, a pyradazine group, a quinolinyl group, an isoquinoline group, an acridyl group and the like, and compounds having the following structural formulas are preferred, but are not limited thereto.

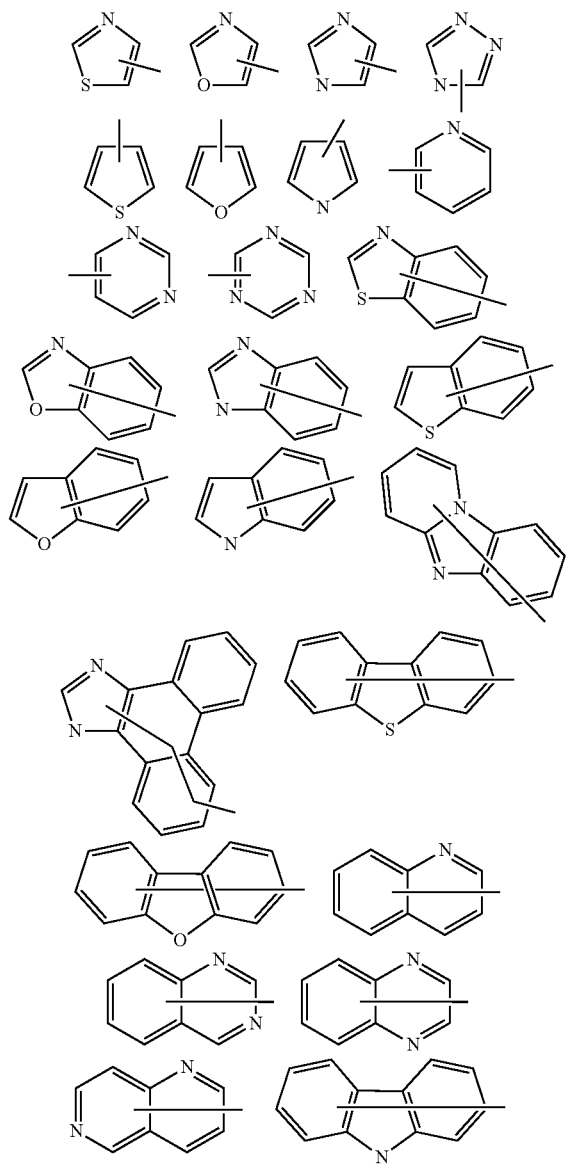

Examples of the halogen group include fluorine, chlorine, bromine, iodine and the like, but are not limited thereto.

Specific examples of the arylene group include a phenylene group, a biphenylene group, a naphthalene group, a binaphthalene group, an anthracenylene group, a fluorenylene group, a chrysenylene group, a phenanthrenylene group and the like, but are not limited thereto.

Examples of the heterocycloalkyl group include a ring group comprising a heterogeneous element such as N, S or O.

Further, as used herein, the term "substituted or unsubstituted" means that a group is substituted with one or more substituent groups selected from the group consisting of deuterium, a halogen group, an alkyl group, an alkenyl group, an alkoxy group, a silyl group, an arylalkenyl group, an aryl group, a heteroaryl group, a carbazole group, an arylamine group, a fluorenyl group which is unsubstituted or substituted with an aryl group, and a nitrile group, or has no substituent group.

R1 to R9 in Formula 1, L, Ar1, Ar2 and A may be further substituted with an additional substituent group, and examples thereof include a halogen group, an alkyl group, an alkenyl group, an alkoxy group, a silyl group, an arylalkenyl group, an aryl group, a heteroaryl group, a carbazole group, an arylamine group, a fluorenyl group which is unsubstituted or substituted with an aryl group, a nitrile group, and the like, but are not limited thereto.

Preferred specific examples of the compound represented by Formula 1 comprise the following compounds, but are not limited thereto.

[Formula 1-1]

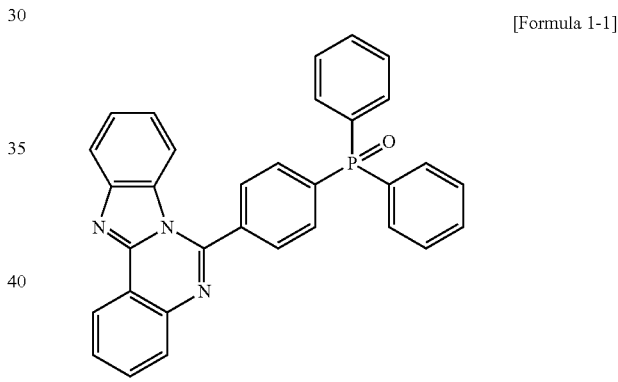

[Formula 1-2]

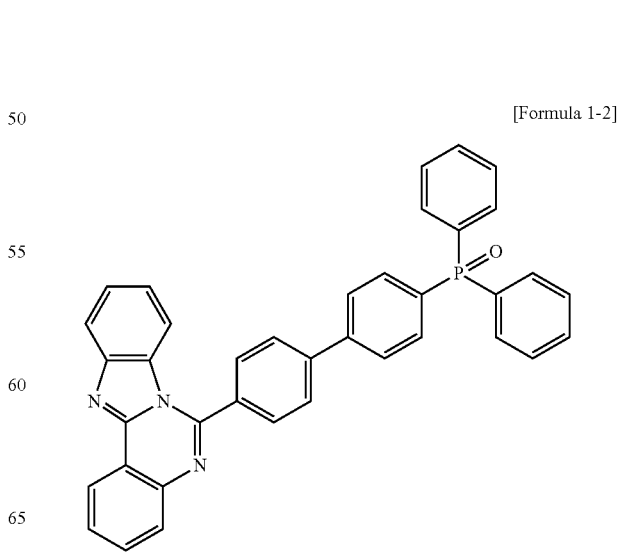

[Formula 1-3]
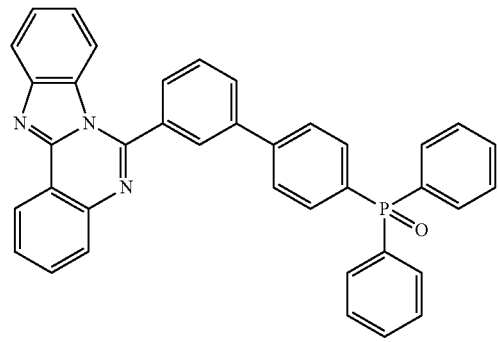
[Formula 1-4]
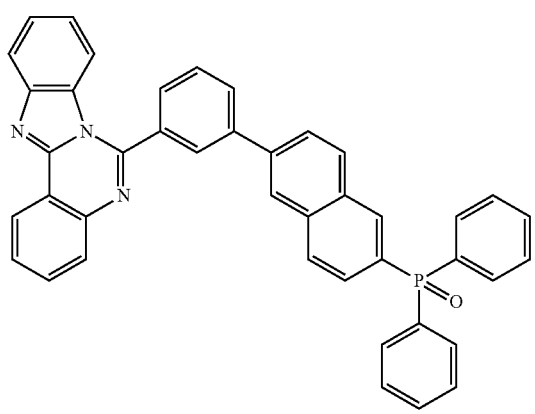
[Formula 1-5]
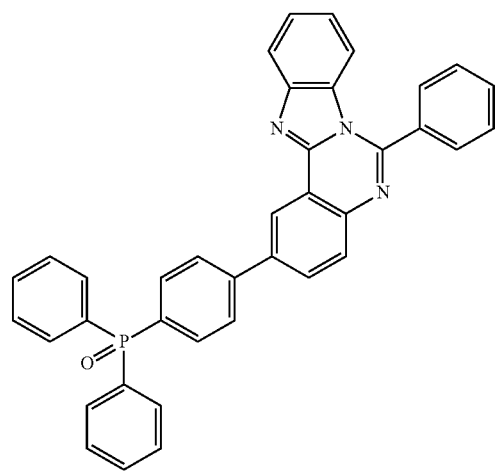
[Formula 1-6]
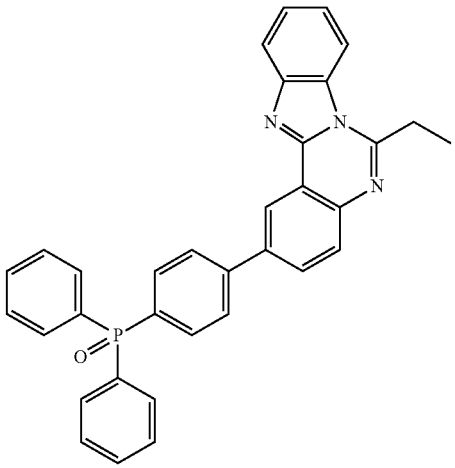
[Formula 1-7]
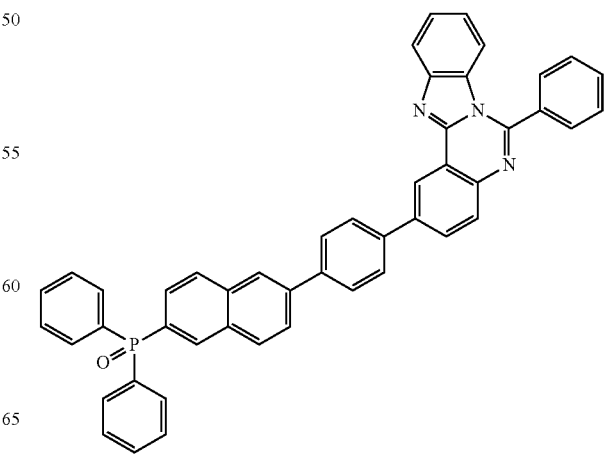
[Formula 1-8]

[Formula 1-9]
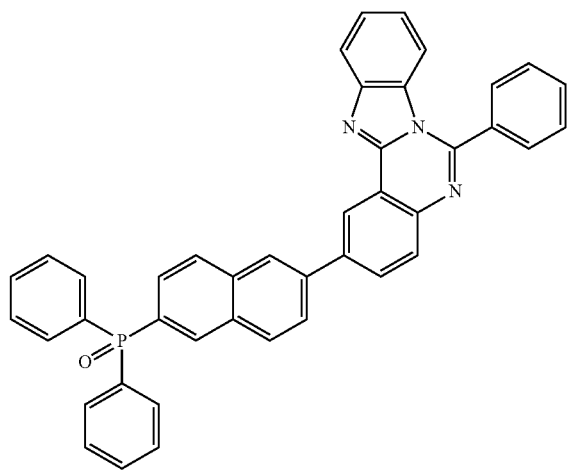
[Formula 1-10]
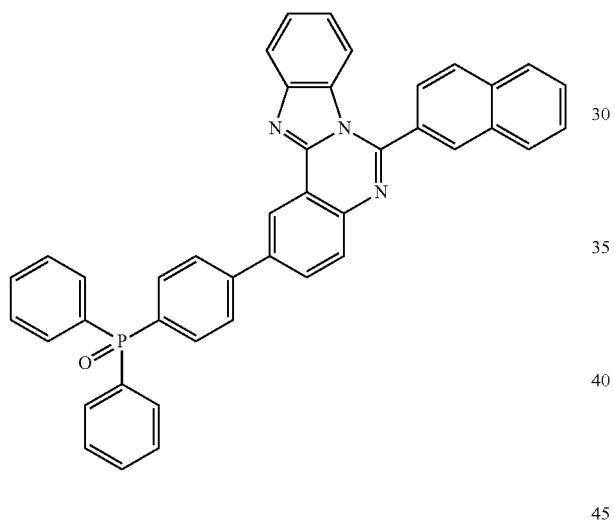
[Formula 1-11]
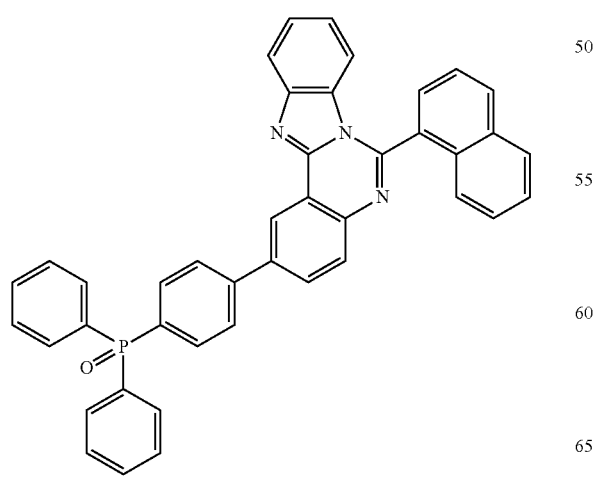
[Formula 1-12]
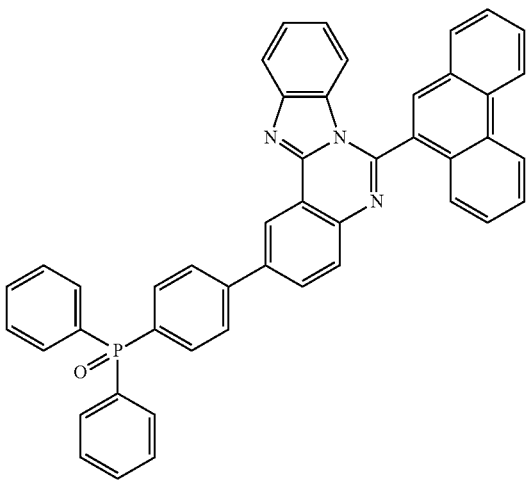
[Formula 1-13]
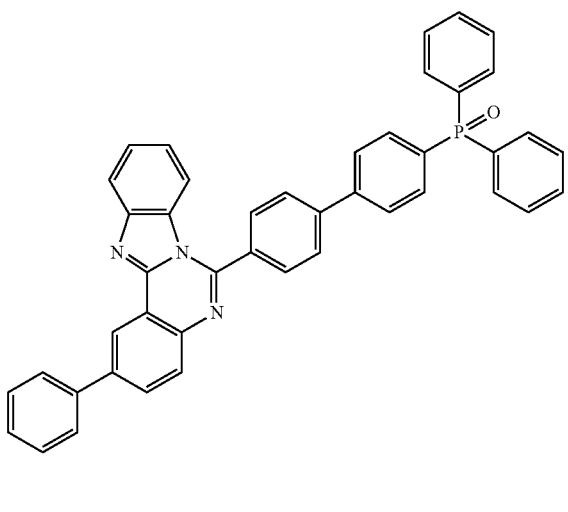
[Formula 1-14]
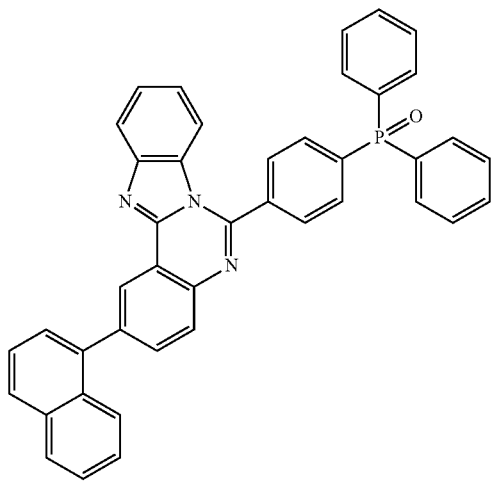

[Formula 1-15]
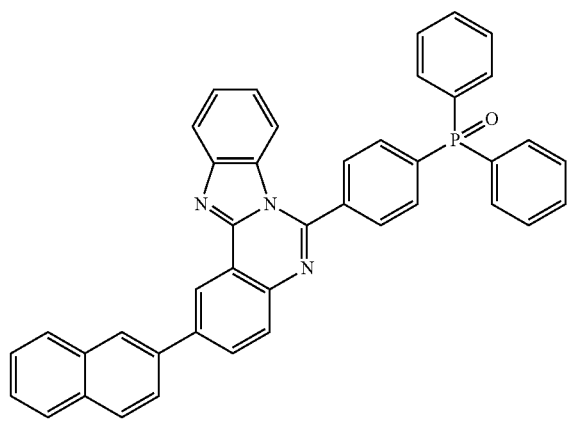
[Formula 1-16]
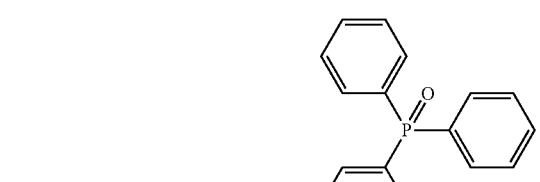
[Formula 1-17]
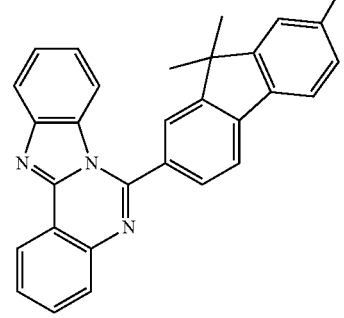
[Formula 1-18]
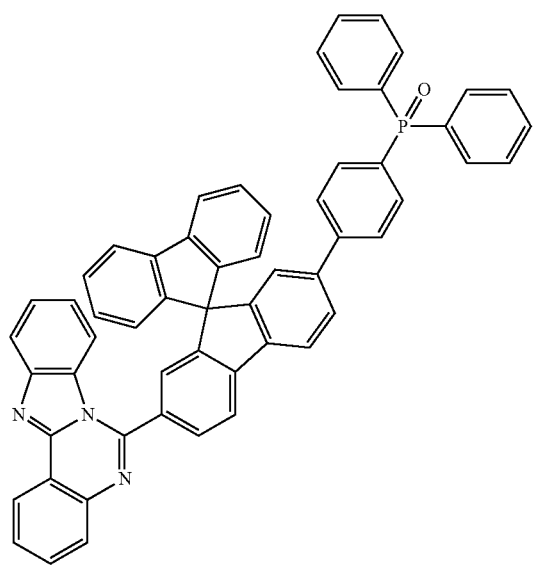
[Formula 1-19]
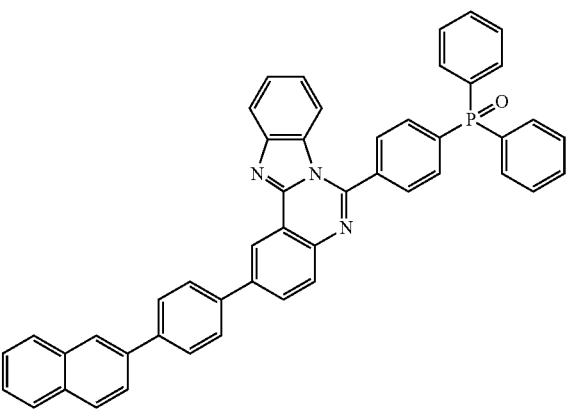
[Formula 1-20]
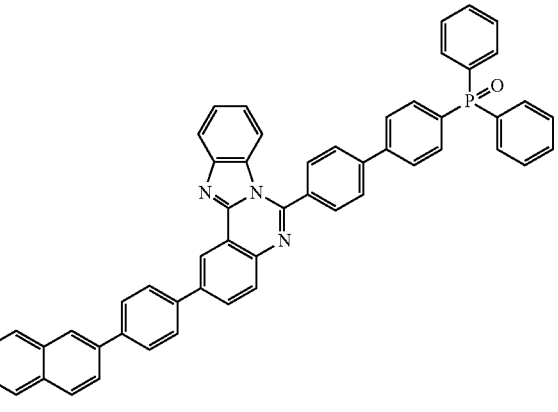

[Formula 1-21]
[Formula 1-22]
[Formula 1-23]
[Formula 1-24]
[Formula 1-25]
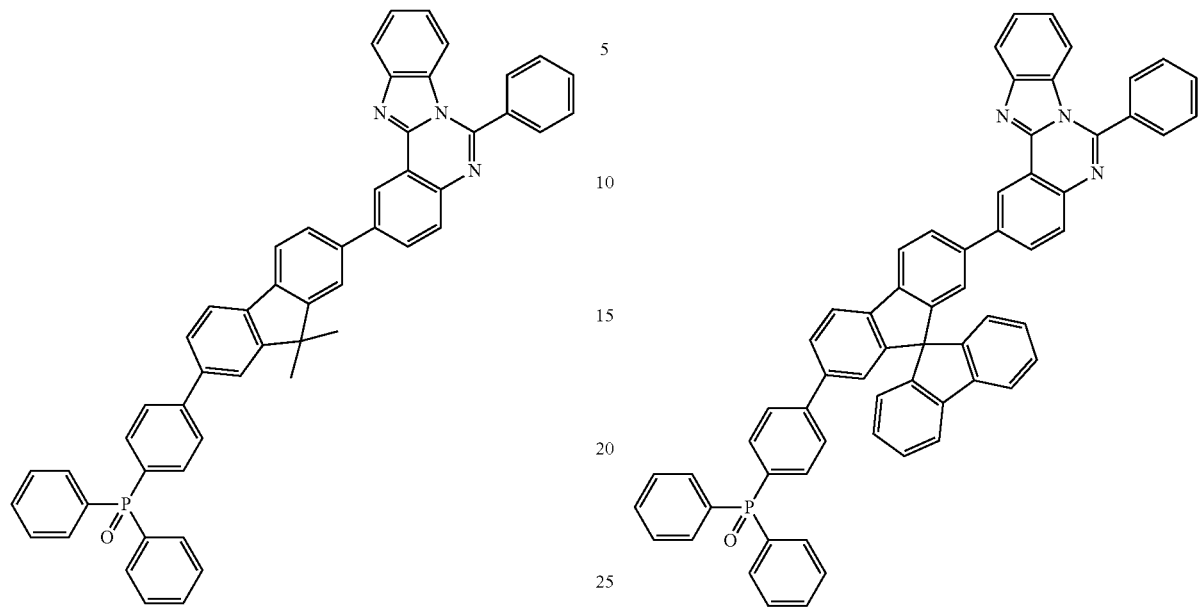
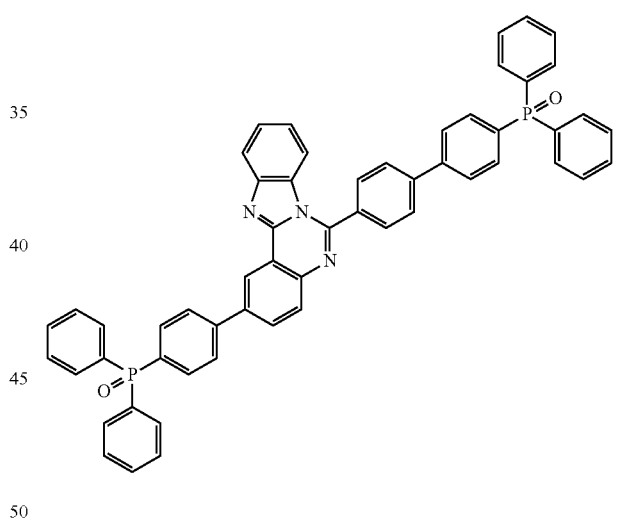
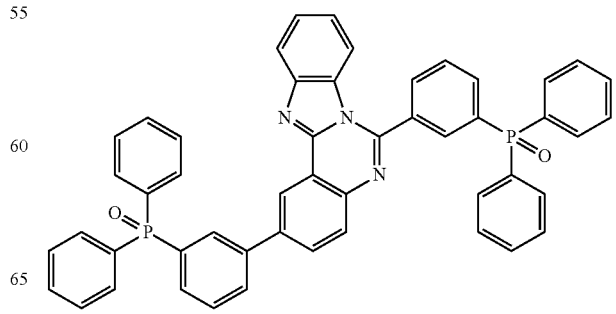

[Formula 1-26]

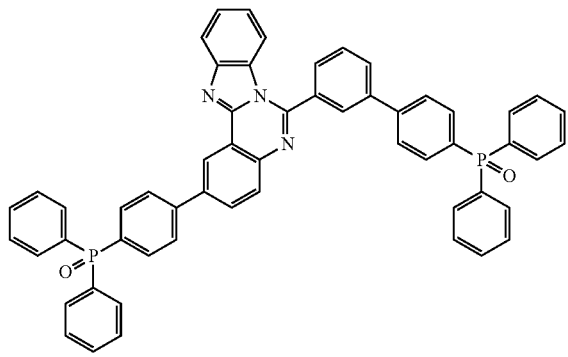

Hereinafter, a method for preparing the compound represented by Formula 1 will be described.

The compound represented by Formula 1 may be prepared by using general methods known in the art, such as condensation reaction, Suzuki coupling reaction and the like.

The compounds represented by Formula 1 may have properties appropriate for use as an organic material layer used in an organic light emitting device by introducing various substituents into a core structure represented in the Formula. The compound represented by Formula 1 may show properties even when used in any layer of the organic light emitting device, but particularly, the following characteristics may be exhibited.

The compounds into which a substituted or unsubstituted arylamine group is introduced are appropriate as a material for a light emitting layer and a hole injection and hole transporting layer, and the compounds into which a heterocyclic group comprising N is introduced are appropriate as a material for an electron injection layer, an electron transferring layer and a hole blocking layer.

The conjugation length of the compound has a close relationship with an energy band gap. Specifically, the energy band gap is reduced as the conjugation length of the compound increases. As described above, the cores of the compounds represented by Formula 1 comprises a limited conjugation and thus have properties from a small energy band gap to a large energy band gap.

In addition, a compound having intrinsic properties of a substituent group introduced may be synthesized by introducing various substituent groups into the core structure as described above. For example, hole injection layer materials and hole transporting layer materials which are used during the manufacture of an organic light emitting device have an energy level enough to transfer holes along the HOMO, and may become a compound capable of having an energy level enough to prevent the movement of electrons flowing along the LUMO from the light emitting layer. In particular, the core structure of the present compound shows stable properties for electrons, thereby contributing to the improvement in the service life of the device. Derivatives produced by introducing substituents so as to be used in the light emitting layer and electron transport layer material may be prepared such that various arylamine-based dopants, aryl-based dopants, dopants containing metals and the like have a suitable energy band gap.

Furthermore, it is possible to precisely control the energy band gap by introducing various substituent groups into the core structure, and properties at the interface between organic materials are improved, thereby making it possible to use the material in various fields.

Meanwhile, the compounds represented by Formula 1 have a high glass transition temperature (Tg), and thus have excellent thermal stability. The improvement in thermal stability is an important factor which provides the driving stability to a device.

Further, the organic electronic device according to the present invention is an organic electronic device comprising a first electrode, a second electrode, and one or more organic material layers disposed between the first electrode and the second electrode, and one or more layers of the organic material layers comprise the compound represented by Formula 1.

The organic electronic device of the present invention may be manufactured by typical manufacturing methods of an organic electronic device and materials, except that one or more organic material layers are formed by using the above-described compounds.

The compound of Formula 1 may be formed as an organic material layer by using a vacuum deposition method as well as a solution coating method during the manufacture of an organic electronic device. Herein, the solution coating method means spin coating, dip coating, inkjet printing, screen printing, a spray method, roll coating and the like, but is not limited thereto.

The organic material layer of the organic electronic device of the present invention may be composed of a mono-layer structure, but may be composed of a multi-layer structure in which two or more organic material layers are stacked. For example, the organic electronic device of the present invention may have a structure comprising a hole injection layer, a hole transporting layer, a light emitting layer, an electron transporting layer, an electron injection layer and the like as an organic material layer. However, the structure of the organic electronic device is not limited thereto, and may comprise the fewer number of organic material layers.

Accordingly, in the organic electronic device of the present invention, the organic material layer may comprise one or more layers of a hole injection layer, a hole transporting layer, and a layer which injects and transports holes simultaneously, and one or more layers of the layers may comprise the compound represented by Formula 1.

In addition, the organic material layer may comprise a light emitting layer, and the light emitting layer may comprise the compound represented by Formula 1.

Furthermore, the organic material layer may comprise one or more layers of an electron transporting layer, an electron injection layer, and a layer which transports and injects electrons simultaneously, and one or more layers of the layers may comprise the compound represented by Formula 1.

In the organic material layer having the multi-layer structure, the compound of Formula 1 may be comprised in a light emitting layer, a layer which injects/transports holes and emits light simultaneously, a layer which transports holes and emits light simultaneously, or a layer which transports electrons and emits light simultaneously.

For example, the structure of the organic light emitting device of the present invention has the same structure as the structures shown in FIGS. 1 to 4, but is not limited thereto.

FIG. 1 illustrates a structure of an organic light emitting device in which an anode 102, a light emitting layer 105 and a cathode 107 are sequentially stacked on a substrate 101. In the structure, the compound of Formula 1 may be comprised in the light emitting layer 105.

Figure 2:
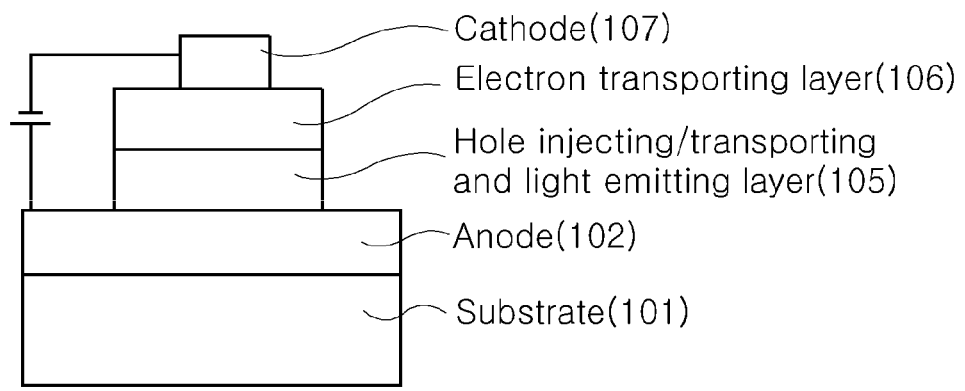
FIG. 2 illustrates a structure of an organic light emitting device in which an anode 102, a hole injection/hole transporting and light emitting layer 105, an electron transporting layer 106 and a cathode 107 are sequentially stacked on a substrate 101.

FIG. 2 illustrates a structure of an organic light emitting device in which an anode 102, a hole injection/hole transporting and light emitting layer 105, an electron transporting layer 106 and a cathode 107 are sequentially stacked on a substrate 101. In the structure, the compound of Formula 1 may be comprised in the hole injection/hole transporting and light emitting layer 105.

Figure 3:
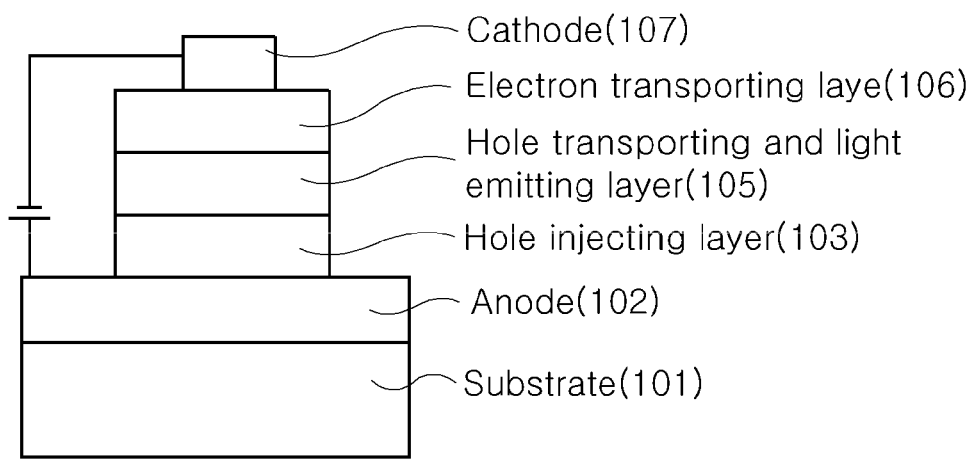
FIG. 3 illustrates a structure of an organic light emitting device in which a substrate 101, an anode 102, a hole injection layer 103, a hole transporting and light emitting layer 105, an electron transporting layer 106 and a cathode 107 are sequentially stacked.

FIG. 3 illustrates a structure of an organic light emitting device in which a substrate 101, an anode 102, a hole injection layer 103, a hole transporting and light emitting layer 105, an electron transporting layer 106 and a cathode 107 are sequentially stacked. In the structure, the compound of Formula 1 may be comprised in the hole injection/hole transporting and light emitting layer 105.

Figure 4:
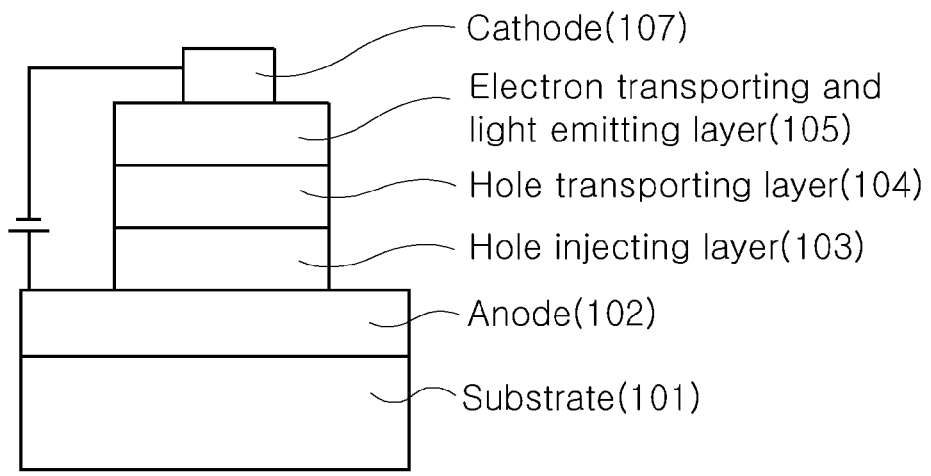
FIG. 4 illustrates a structure of an organic light emitting device in which a substrate 101, an anode 102, a hole injection layer 103, a hole transporting layer 104, an electron transporting and light emitting layer 105 and a cathode 107 are sequentially stacked.

FIG. 4 illustrates a structure of an organic light emitting device in which a substrate 101, an anode 102, a hole injection layer 103, a hole transporting layer 104, an electron transporting and light emitting layer 105 and a cathode 107 are sequentially stacked. In the structure, the compound of Formula 1 may be comprised in the electron transporting and light emitting layer 105.

In the organic electronic device of the present invention, the compound represented by Formula 1 is more preferably comprised in the electron transporting layer, a layer that transports and injects electrons simultaneously or a light emitting layer.

For example, the organic light emitting device according to the present invention may be manufactured by depositing a metal or a metal oxide having conductivity, or an alloy thereof on a substrate to form an anode by a physical vapor deposition (PVD) method such as sputtering or e-beam evaporation, forming an organic material layer which comprises a hole injection layer, a hole transporting layer, a light emitting layer, and an electron transporting layer thereon, and then depositing a material which may be used as the cathode thereon. In addition to these methods, an organic light emitting device may be manufactured by sequentially depositing a cathode material, an organic material layer and an anode material on a substrate.

The organic material layer may be a multi-layer structure comprising the hole injection layer, the hole transporting layer, the light emitting layer, the electron transporting layer and the like, but may be a mono-layer structure without being limited thereto. Further, the organic material layer may be manufactured with fewer layers by using various polymer materials by a solvent process other than a deposition method, for example, methods such as spin coating, dip coating, doctor blading, screen printing, inkjet printing, a thermal transfer method or the like.

It is preferred that as the anode material, materials having a high work function are typically used so as to facilitate the injection of holes into the organic material layer. Specific examples of the anode material which may be used in the present invention comprise metals such as vanadium, chromium, copper, zinc, and gold or alloys thereof; metal oxides such as zinc oxide, indium oxide, indium tin oxide (ITO), and indium zinc oxide (IZO); a combination of metal and oxide such as ZnO:Al or SnO$_2$:Sb; and electrically conductive polymers such as poly(3-methyl compound), poly[3,4-(ethylene-1,2-dioxy)compound](PEDT), polypyrrole, and polyaniline, and the like, but are not limited thereto.

It is preferred that as the cathode material, materials having a low work function are typically used so as to facilitate the injection of electrons into the organic material layer. Specific examples of the cathode material include metals such as magnesium, calcium, sodium, potassium, titanium, indium, yttrium, lithium, gadolinium, aluminum, silver, tin and lead or alloys thereof; multilayer structured materials such as LiF/Al or LiO$_2$/Al, and the like, but are not limited thereto.

The hole injection material is a material facilitating the injection of holes from the anode at low voltage. The highest occupied molecular orbital (HOMO) of the hole injection material is preferably between the work function of the anode materials and the HOMO of the neighboring organic material layer. Specific examples of the hole injection material include metal porphyrine, oligothiophene, arylamine-based organic materials, hexanitrile hexaazatriphenylene-based organic materials, quinacridone-based organic materials, perylene-based organic materials, antraquinone, and polyaniline-based and polycompound-based conductive polymers, and the like, but are not limited thereto.

The hole transporting material is suitably a material having high hole mobility, which may receive and transfer holes from the anode or the hole injection layer to the light emitting layer. Specific examples thereof include arylamine-based organic materials, conductive polymers, block copolymers having both conjugated portions and non-conjugated portions, and the like, but are not limited thereto.

The light emitting material is a material capable of emitting light in a visible light region by accepting and recombining holes from the hole transporting layer and electrons from the electron transporting layer, respectively, and preferably a material having high quantum efficiency for fluorescence and phosphorescence. Specific examples thereof include 8-hydroxy-quinoline-aluminum complex (Alq$_3$); carbazole-based compounds; dimerized styryl compounds; BAlq; 10-hydroxybenzoquinoline-metal compounds; benzoxazole-based, benzthiazole-based and benzimidazole-based compounds; poly(p-phenylenevinylene)(PPV)-based polymers; spiro compounds; and polyfluorene, rubrene and the like, but are not limited thereto.

The electron transporting material is suitably a material having high electron mobility, which may receive and transfer electrons from the cathode to the light emitting layer. Specific examples thereof include aluminum complexes of 8-hydroxyquinoline; complexes comprising Alq$_3$; organic radical compounds; hydroxyflavone-metal complexes, and the like, but are not limited thereto.

The organic light emitting device according to the present invention may be a top emission type, a bottom emission type or a both side emission type according to the materials used.

The compound according to the present invention may be operated by the principles similar to the principles, which are applied to organic light emitting devices, even in organic electronic devices comprising organic solar cells, organic photoconductors, organic transistors, and the like.

Accordingly, the organic electronic device may be selected from the group consisting of an organic light emitting device, an organic phosphorescence device, an organic solar cell, an organic photoconductor (OPC) and an organic transistor.

BEST MODE

Hereinafter, preferred Examples will be provided for better understanding of the present invention. However, the following Examples are for illustrative purposes only, and the scope of the present invention are not limited thereto in any manner.

EXAMPLE
Preparation Example 1
Preparation of Compound Represented by Formula 1-2
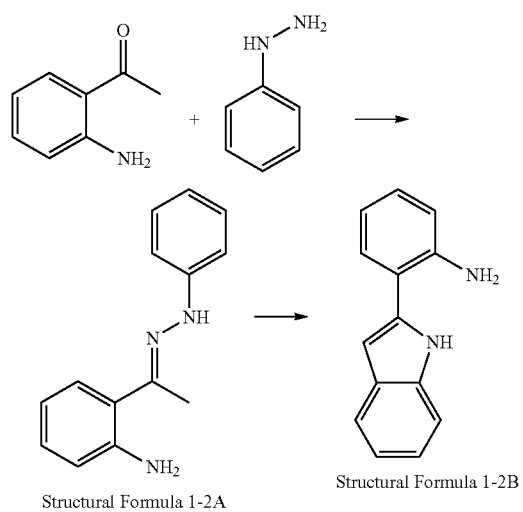
Structural Formula 1-2A
Structural Formula 1-2B
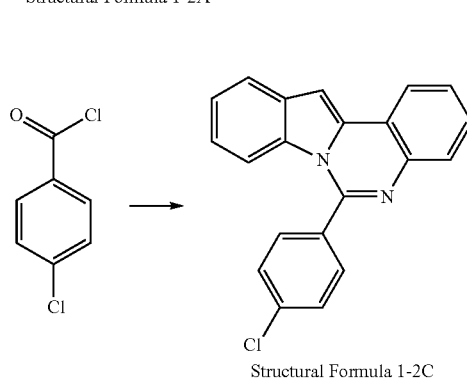
Structural Formula 1-2C
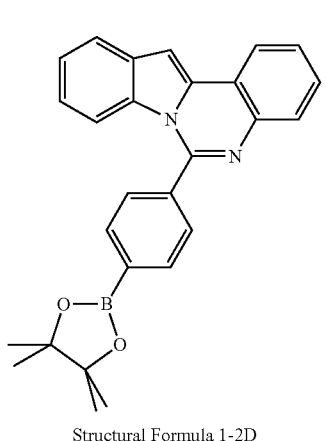
Structural Formula 1-2D
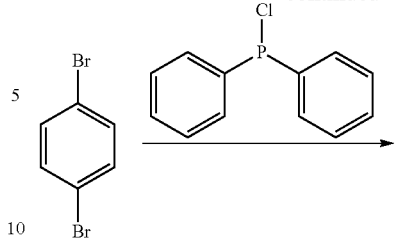
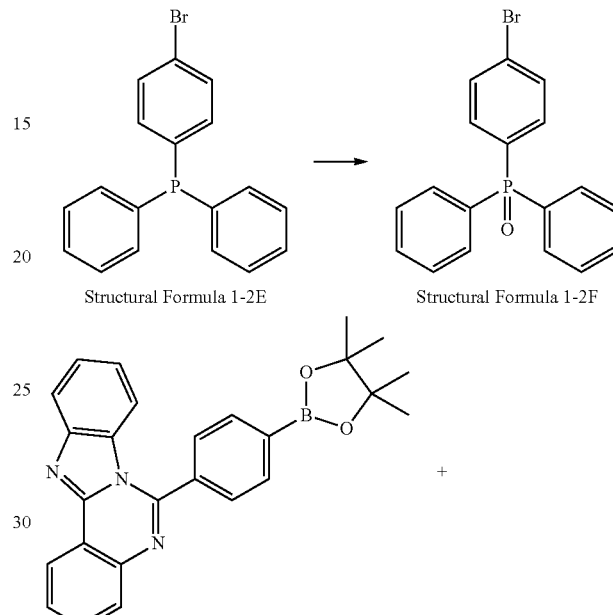
Structural Formula 1-2E
Structural Formula 1-2F
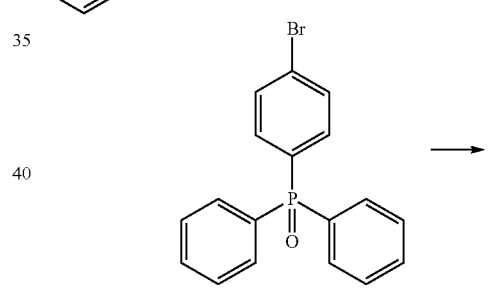
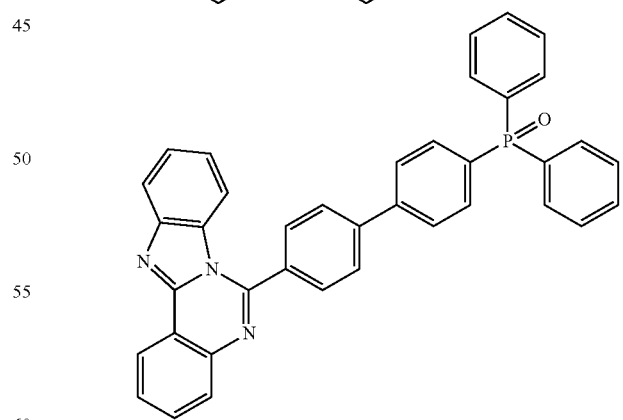
Structural Formula 1-2
Preparation of Structural Formula 1-2A
2'-aminoacetophenone (9.6 mL, 80 mmol) and phenylhydrazine (15 g, 103.7 mmol) were put into ethanol (100 mL)

and glacial acetic acid (30 mL) and the mixture was heated while stirring for 5 hr. The mixture was cooled to normal temperature, and the solid produced was filtered and washed with ethanol (30 mL) and then dried under vacuum to obtain Structural Formula 1-2A (14 g, yield 83%).

MS: [M+H]+=226

Preparation of Structural Formula 1-2B

Phosphorus pentoxide (8.4 g, 58.7 mmol) was put into methane sulfonic acid (100 mL) and the mixture was stirred at 80° C. until the phosphorus pentoxide was completely dissolved. Structural Formula 1-2A (6.3 g, 28 mmol) was slowly added thereto, and then the mixture was stirred at 90° C. for 3 hr and cooled to normal temperature. The reaction solution was put into a sodium hydroxide aqueous solution at 0° C., the mixture was stirred for 10 min, and then the solid produced was filtered. The solid was washed with distilled water and dried under vacuum to obtain Structural Formula 1-2B (4 g, yield 69%).

MS: [M+H]+=209

Preparation of Structural Formula 1-2C

Structural Formula 1-2B (4 g, 19.2 mmol) and 4-chlorobenzoyl chlorides (2.4 mL, 19.2 mmol) were put into p-toluene sulfonic acid (50 mL) and the mixture was heated while stirring for 5 hr. The mixture was cooled to 50° C., and then 2,3-dichloro-5,6-dicyano-1,4-benzoquinone (DDQ) (4.8 g, 21.1 mmol) was slowly added thereto. The mixture was heated while stirring for 2 hr and then cooled to normal temperature, and a potassium carbonate aqueous solution was slowly added thereto. The mixture was stirred for 30 min, the water layer was removed, and the solid produced was filtered. The filtered solid was recrystallized in chloroform to obtain Structural Formula 1-2C (5 g, 79%).

MS: [M+H]=328

Preparation of Structural Formula 1-2D

Structural Formula 1-2C (13 g, 40 mmol), bis(pinacolato)diboron (12 g, 47 mmol) and potassium acetate (12 g, 118 mmol) were dissolved in dioxane (150 mL), the mixture was heated to 50° C., Pd(DBA)$_2$ (0.23 g, 0.4 mmol) and P(Cy)$_3$ (0.22 g, 0.8 mmol) were added thereto, and the resulting mixture was heated while stirring for 12 hr. The reaction solution was cooled to room temperature, distilled water (100 mL) was added thereto, and the mixture was extracted with methylene chloride (100 mL×3). The organic layer was concentrated and recrystallized with ethanol to obtain Structural Formula 1-2D (14 g, yield 90%).

MS: [M+H]$^+$=420

Preparation of Structural Formula 1-2E

Dibromobenzene (20 g, 85 mmol) was dissolved in tetrahydrofuran (100 ml), and then the mixture was cooled to 78° C. n-BuLi (2.5 M, 37 ml, 93 mmol) was slowly added dropwise thereto, and then the resulting mixture was stirred for 30 min. Chlorodiphenylphosphine (17 g, 76 mmol) was slowly added dropwise thereto, the mixture was stirred for 3 hr and heated to normal temperature, and then water (100 ml) was added thereto and the resulting mixture was extracted with tetrahydrofuran. The organic layer was concentrated and recrystallized with hexane to obtain Structural Formula 1-2E (20 g, yield 70%).

MS: [M+H]$^+$=342

Preparation of Structural Formula 1-2F

The Structural Formula 1-2E (20 g, 58 mmol) was dissolved in trichloromethane (200 ml), a hydrogen peroxide solution (20 ml) was added thereto, and then the resulting mixture was stirred for 12 hr. MgSO$_4$ was added thereto and the mixture was stirred to remove water, the resulting mixture was filtered, concentrated and recrystallized with hexane to obtain Structural Formula 1-2F (18 g, yield 85%).

MS: [M+H]$^+$=358

Preparation of Formula 1-2

Structural Formula 1-2D (9.4 g, 22.4 mmol) and Structural Formula 1-2F (8 g, 22.4 mmol) were heated until they were completely dissolved in tetrahydrofuran (200 ml), then 100 ml of a 2 M potassium carbonate aqueous solution was added to the solution, Pd(PPh$_3$)$_4$ (0.26 g, 0.22 mmol) was added thereto, and the mixture was stirred for 12 hr. The mixture was cooled to normal temperature, the water layer was removed, and the solid produced was filtered. The solid filtered was recrystallized with tetrahydrofuran and acetone to obtain Formula 1-2 (8 g, yield 62%).

MS: [M+H]$^+$=572

Preparation Example 2

Preparation of Compound Represented by Formula 1-4

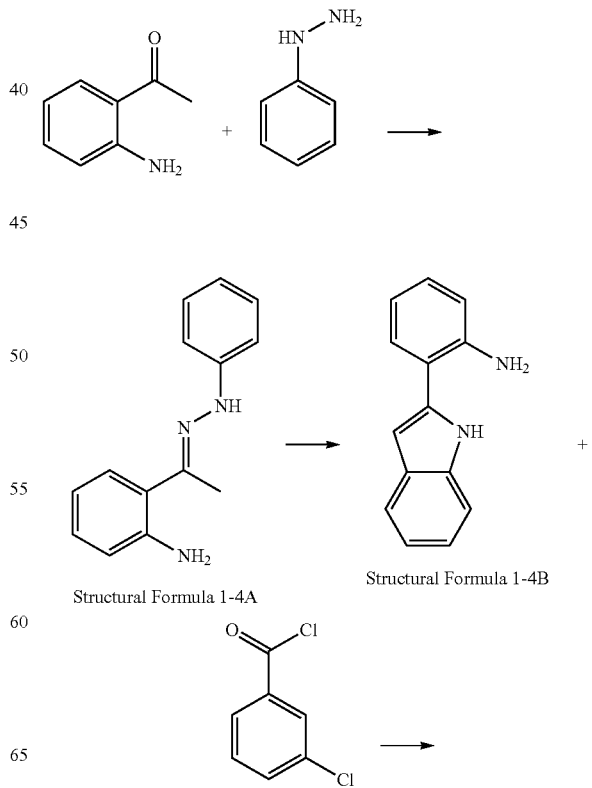

Structural Formula 1-4A

Structural Formula 1-4B

-continued
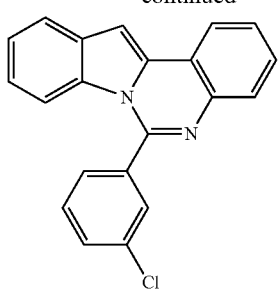
Structural Formula 1-4C
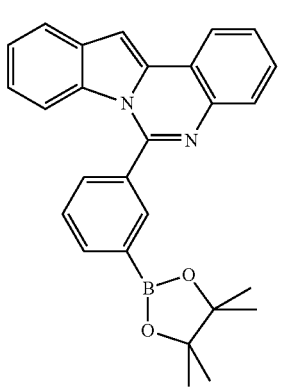
Structural Formula 1-4D
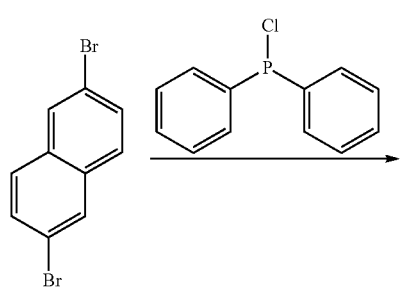
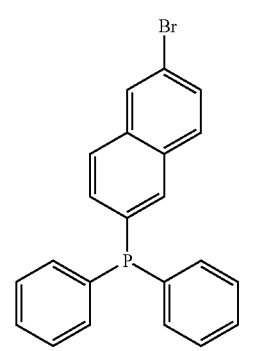
Structural Formula 1-4E
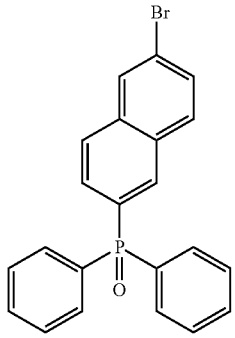
Structural Formula 1-4F
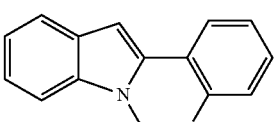
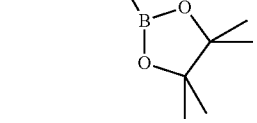
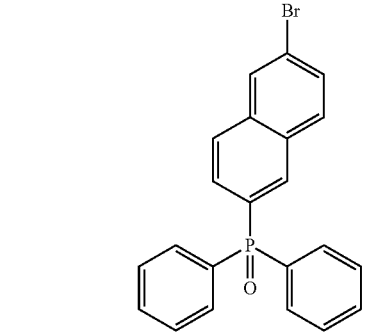
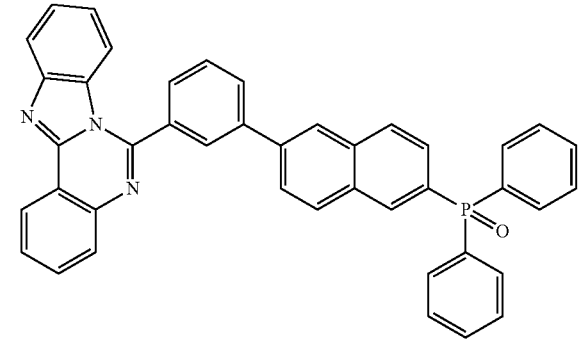
Structural Formula 1-4
Preparation of Structural Formula 1-4C
Structural Formula 1-4C was obtained in the same manner as in the preparation method of Structural Formula 1-2C, except that 3-chlorobenzoyl chloride was used instead of 4-chlorobenzoyl chloride.
MS: $[M+H]^+=328$ Preparation of Structural Formula 1-4D Structural Formula 1-4D was obtained in the same manner as in the preparation method of Structural Formula 1-2D, except that Structural Formula 1-4C was used instead of Structural Formula 1-2C.

MS: [M+H]$^+$=420

Preparation of Structural Formula 1-4E

Structural Formula 1-4E was obtained in the same manner as in the preparation method of Structural Formula 1-2E, except that 2,6-dibromonaphthalene was used instead of 1,4-dibromobenzene.

MS: [M+H]$^+$=392

Preparation of Structural Formula 1-4F

Structural Formula 1-4F was obtained in the same manner as in the preparation method of Structural Formula 1-2F, except that Structural Formula 1-4E was used instead of Structural Formula 1-2E.

MS: [M+H]$^+$=408

Preparation of Formula 1-4

Formula 1-4 was obtained in the same manner as in the preparation method of Formula 1-2, except that Structural Formula 1-4D and Structural Formula 1-4F were used instead of Structural Formula 1-2D and Structural Formula 1-2F, respectively.

MS: [M+H]$^+$=622

Preparation Example 3

Preparation of Compound Represented by Formula 1-7

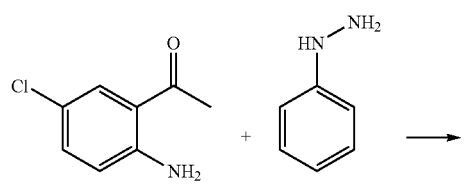

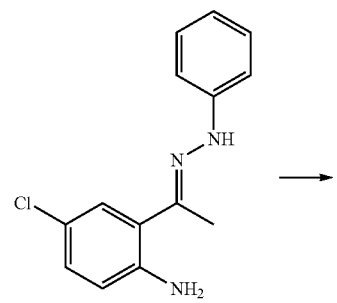

Structural Formula 1-7A

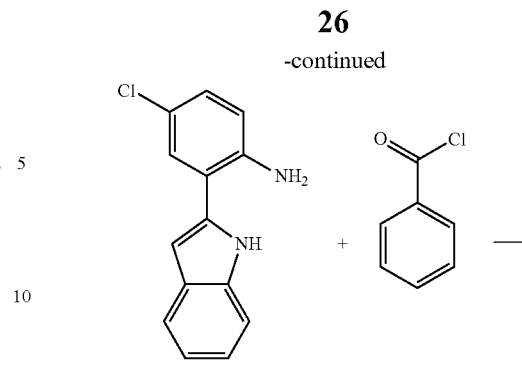

Structural Formula 1-7B

Structural Formula 1-7C

Structural Formula 1-7D

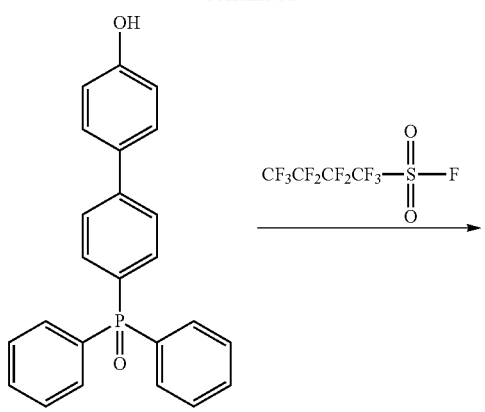

Structural Formula 1-7E

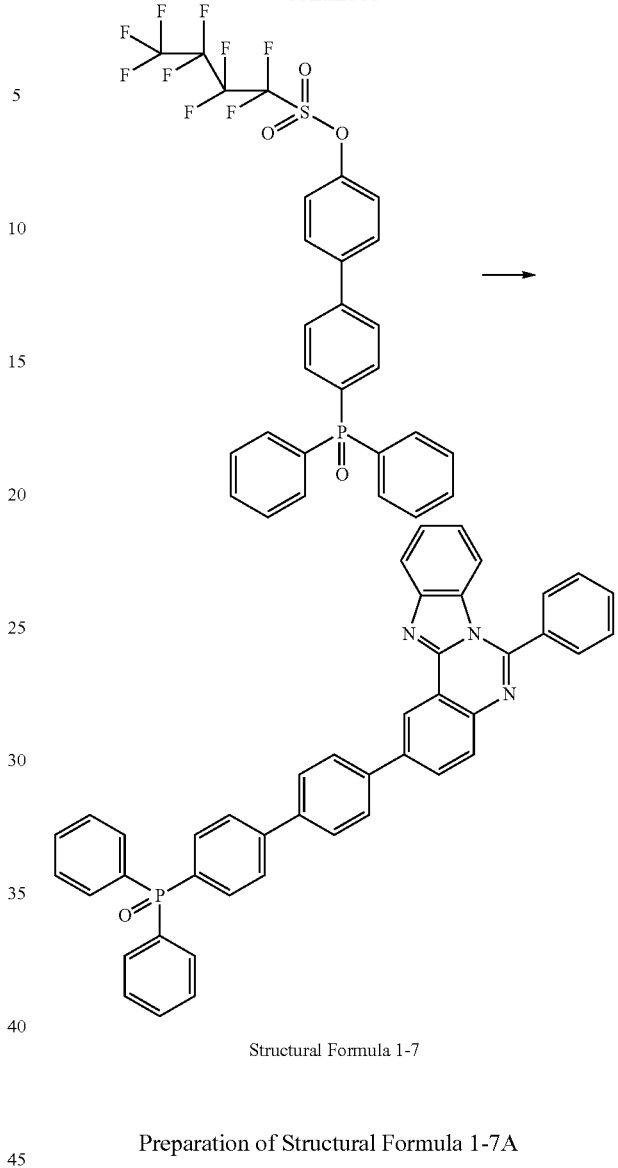

Structural Formula 1-7

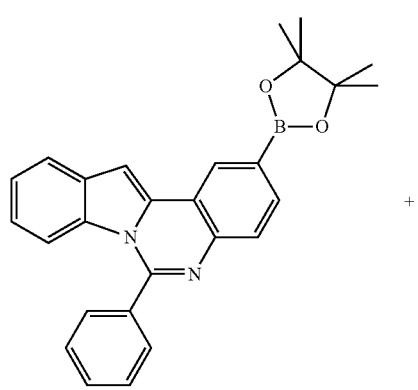

+

Preparation of Structural Formula 1-7A

Structural Formula 1-7A was obtained in the same manner as in the preparation method of Structural Formula 1-2A, except that 2'-amino-5-chloroacetophenone was used instead of 2'-aminoacetophenone.

MS: $[M+]^+=260$

Preparation of Structural Formula 1-7B

Structural Formula 1-7B was obtained in the same manner as in the preparation method of Structural Formula 1-2B, except that Structural Formula 1-7A was used instead of Structural Formula 1-2A.

MS: $[M+H]^+=243$

Preparation of Structural Formula 1-7C

Structural Formula 1-7C was obtained in the same manner as in the preparation method of Structural Formula 1-2C, except that benzoyl chloride was used instead of 4-chlorobenzoyl chloride.

MS: $[M+H]^+=329$

Preparation of Structural Formula 1-7D

Structural Formula 1-7D was obtained in the same manner as in the preparation method of Structural Formula 1-2D, except that Structural Formula 1-7C was used instead of Structural Formula 1-2C.

MS: [M+H]$^+$=421

Preparation of Structural Formula 1-7E

Structural Formula 1-2F (8 g, 22.4 mmol) and 4-hydroxyphenylboronic acid (3.1 g, 22.4 mmol) were heated until they were completely dissolved in tetrahydrofuran (200 ml), then 100 ml of a 2 M potassium carbonate aqueous solution was added to the solution, Pd(PPh$_3$)$_4$ (0.26 g, 0.22 mmol) was added thereto, and the mixture was stirred for 12 hr. The mixture was cooled to normal temperature, an organic layer was extracted, and then a solid produced by distilling off the solvent was filtered. The solid filtered was recrystallized with tetrahydrofuran and hexane to obtain Structural Formula 1-7E (7 g, yield 84%).

MS: [M+H]$^+$=371

Preparation of Structural Formula 1-7F

Structural Formula 1-7E (7 g, 18.9 mmol) was dissolved in acetonitrile (200 ml), perchlorobutane sulfonylchloride (2.9 g, 20.8 mmol) and 100 ml of a 2 M potassium carbonate aqueous solution were added thereto and heated, and then the mixture was stirred for 12 hr. The mixture was cooled to normal temperature, an organic layer was extracted, and then a solid produced by distilling off the solvent was filtered. The solid filtered was recrystallized with chloroform and hexane to obtain Structural Formula 1-7F (9.5 g, yield 75%).

MS: [M+H]$^+$=653

Preparation of Formula 1-7

Formula 1-7 was obtained in the same manner as in the preparation method of Formula 1-2, except that Structural Formula 1-7D and Structural Formula 1-7F were used instead of Structural Formula 1-2D and Structural Formula 1-2F, respectively.

MS: [M+H]$^+$=648

Preparation Example 4

Preparation of Compound Represented by Formula 1-24

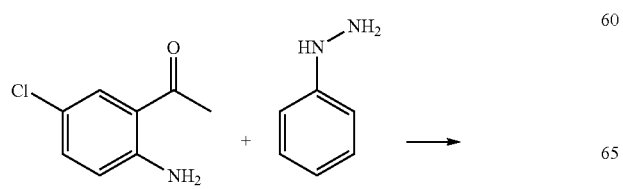

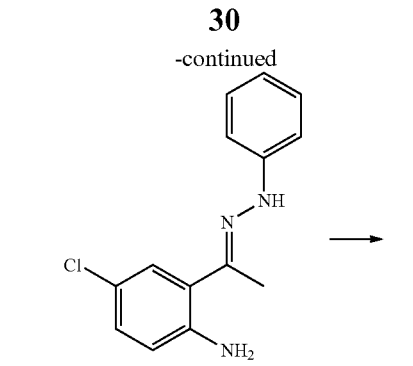

Structural Formula 1-7A

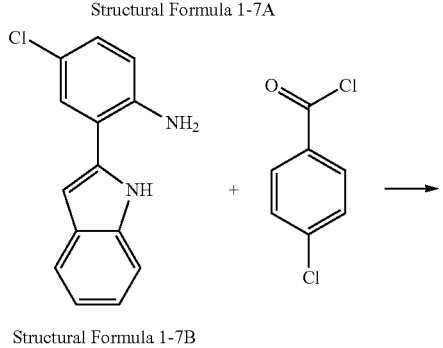

Structural Formula 1-7B

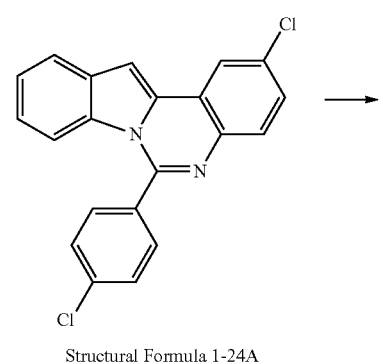

Structural Formula 1-24A

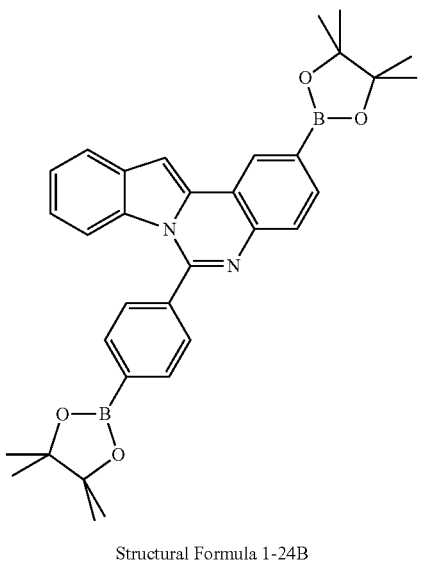

Structural Formula 1-24B

-continued

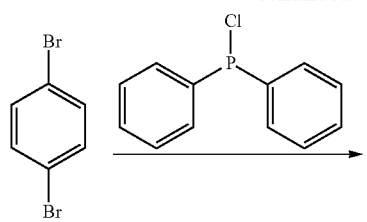

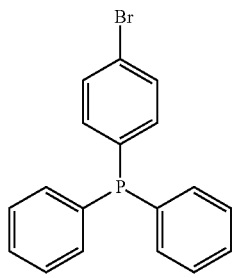

Structural Formula 1-2E

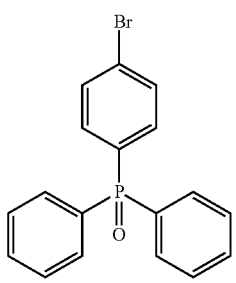

Structural Formula 1-2F

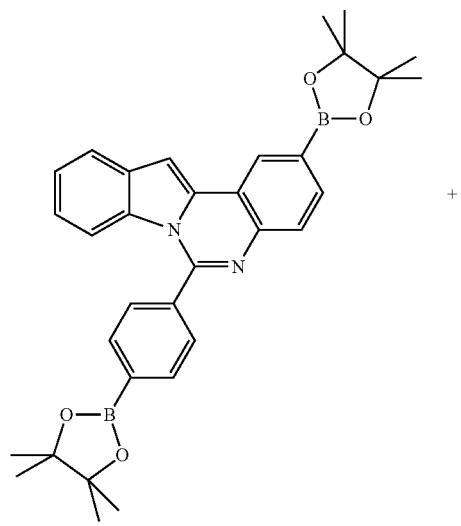

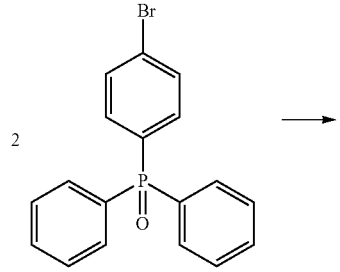

-continued

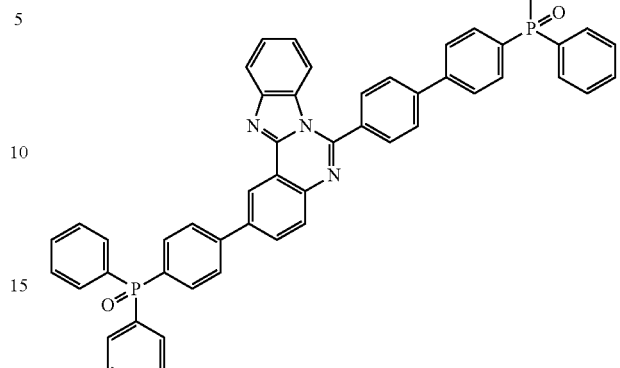

Structural Formula 1-24

Preparation of Structural Formula 1-24A

Structural Formula 1-24A was obtained in the same manner as in the preparation method of Structural Formula 1-7C, except that 4-chlorobenzoyl chloride was used instead of benzoyl chloride.
MS: [M+H]$^+$=363

Preparation of Structural Formula 1-24B

Structural Formula 1-24B was obtained in the same manner as in the preparation method of Structural Formula 1-7D, except that Structural Formula 1-24A was used instead of Structural Formula 1-7C.
MS: [M+H]$^+$=547

Preparation of Formula 1-24

Formula 1-24 was obtained in the same manner as in the preparation method of Formula 1-2, except that Structural Formula 1-24B was used instead of Structural Formula 1-2D.
MS: [M+H]$^+$=848

Example 1

A glass substrate (corning 7059 glass), on which ITO (indium tin oxide) was coated to a thickness of 1,000 to form a thin film, was put in a distilled water in which a dispersing agent was dissolved, and then washed using ultrasonic waves. A product manufactured by Fischer Co. was used as a detergent, and distilled water twice filtered by a filter manufactured by Millipore Co. was used as the distilled water. After ITO was washed for 30 min, ultrasonic washing was twice conducted by using distilled water for 10 min. After the washing using distilled water was completed, ultrasonic washing was conducted using isopropyl alcohol, acetone, and methanol solvents in sequence, and drying was then conducted.
Hexanitrile hexaazatriphenylene was vacuum deposited to a thickness of 500 by heating on a transparent ITO electrode, which was thus prepared, so as to form a hole injection layer. NPB (400 Å), which is a material that transports holes, was vacuum deposited thereon, and a compound of host H1 and dopant D1 was vacuum deposited to a thickness of 300 Å as a light emitting layer. Then, the compound of Formula 1-2, which was synthesized in Preparation Example 1, and LIQ were vacuum deposited (to a thickness of 200 Å) by heating as an electron injection and transporting layer. An organic light emitting device was manufactured by sequentially depositing lithium quinolate (LiQ) having a thickness of 12 and aluminum having a thickness of 2,000 on the electron transporting layer to form a cathode.

E1 was used as a Comparative Example of the electron transporting layer.

In the above-described procedure, the deposition rate of organic materials was maintained at 1/sec, while the deposition rates of lithium quinolate and aluminum were maintained at 0.2/sec and 3/sec to 7/sec, respectively.

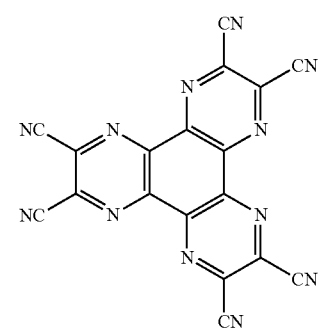

[Hexanitrile hexaazatriphenylene]

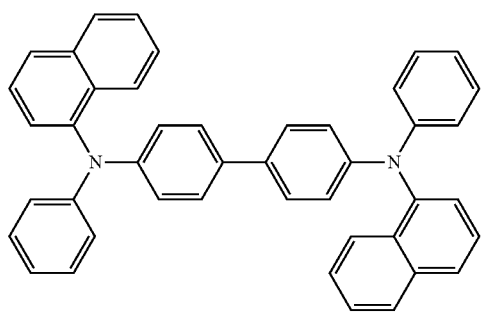

[NPB]

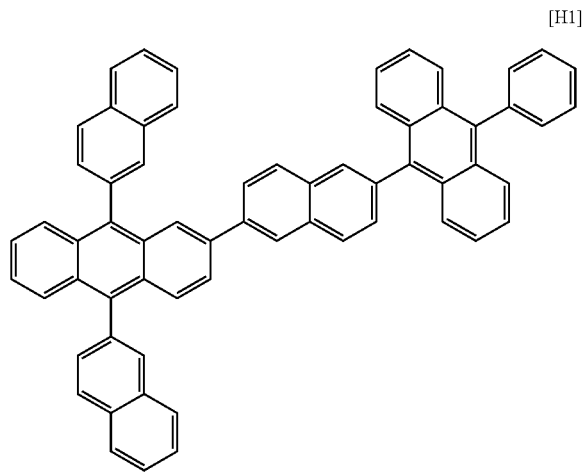

[H1]

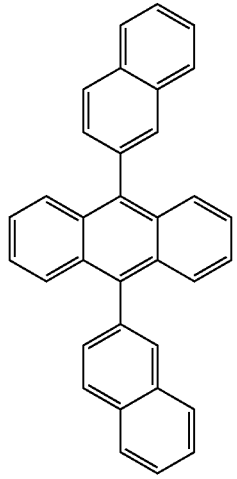

[H2]

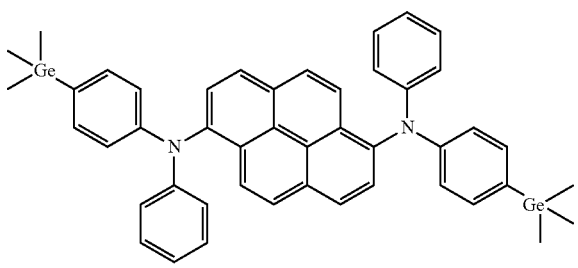

[D1]

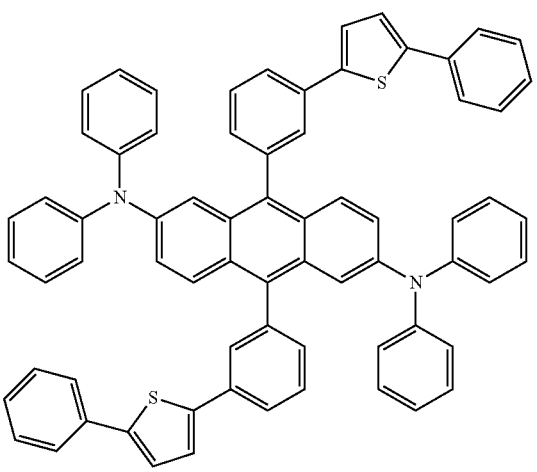

[D2]

-continued

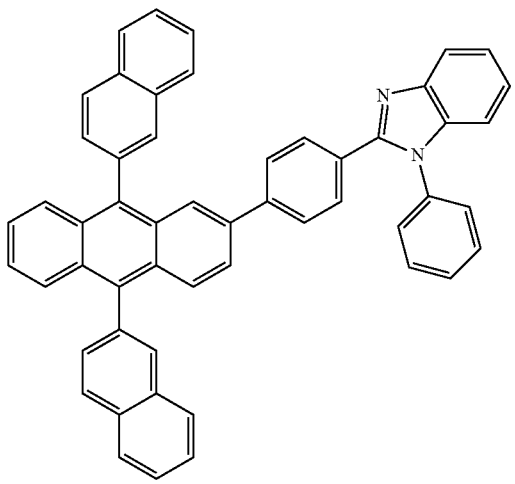

[E1]

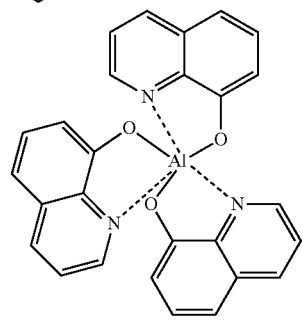

[Alq₃]

Example 2

An experiment was performed in the same manner as in Example 1, except that Formula 1-4 was used as the electron transporting layer instead of Formula 1-2.

Example 3

An experiment was performed in the same manner as in Example 1, except that Formula 1-7 was used as the electron transporting layer instead of Formula 1-2.

Example 4

An experiment was performed in the same manner as in Example 1, except that Formula 1-24 was used as the electron transporting layer instead of Formula 1-2.

Comparative Example 1

An experiment was performed in the same manner as in Example 1, except that E1 was used as the electron transporting layer instead of Formula 1-2.

As in the Example, the results obtained by performing an experiment on an organic light emitting device manufactured by using each compound as a hole transporting layer material are shown in Table 1.

TABLE 1

| Experimental Example (5 mA/cm²) | ETL material | Voltage (V) | Efficiency (cd/A) | Color coordinate (x, y) | Service life (Td5) (hr) |
|---|---|---|---|---|---|
| Comparative Example 1 | E1 | 4.11 | 19.05 | (0.314, 0.650) | 94 |
| Example 1 | Formula 1-2 | 6.28 | 17.09 | (0.315, 0.650) | 590 |
| Example 2 | Formula 1-4 | 5.01 | 19.24 | (0.314, 0.655) | 256 |
| Example 3 | Formula 1-7 | 4.90 | 17.88 | (0.311, 0.654) | 183 |
| Example 4 | Formula 1-24 | 5.07 | 15.63 | (0.315, 0.655) | 309 |

As shown in the results, the new compound according to the present invention may be used as a material for an organic material layer of an organic electronic device comprising an organic light emitting device by introducing various substituent groups and the like. The organic electronic device comprising an organic light emitting device using the compound represented by Formula 1 according to the present invention as a material for an organic material layer shows excellent properties in terms of efficiency, driving voltage, service life and the like.

The invention claimed is:

1. A compound represented by the following Formula 1:

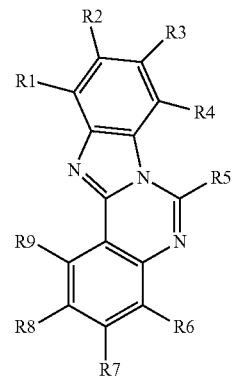

[Formula 1]

wherein
at least one of R5 to R8 is represented by the following Formula 2 and the rest thereof are hydrogen or an aryl group having 6 to 40 carbon atoms;
R1, R2, R3, R4, R6, R7 and R9 are hydrogen;

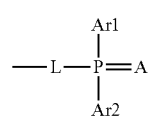

[Formula 2]

L is an arylene group having 6 to 40 carbon atoms which is unsubstituted or substituted with an aryl group having 6 to 40 carbon atoms,
Ar1 and Ar2 are each independently an aryl group having 6 to 40 carbon atoms and
A is O.

2. The compound of claim 1, wherein R5 in Formula 1 is represented by Formula 2.

3. The compound of claim 1, wherein the compound represented by Formula 1 is represented by any one of the following Formulas:
[Formula 1-1]
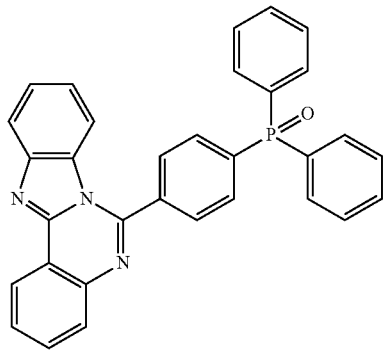
[Formula 1-2]
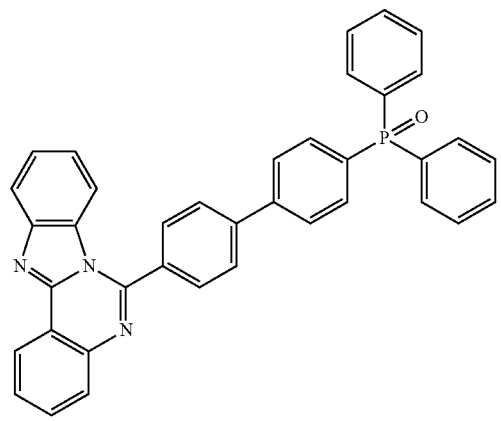
[Formula 1-3]
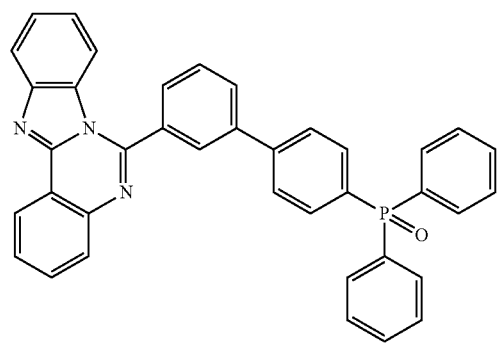
[Formula 1-4]
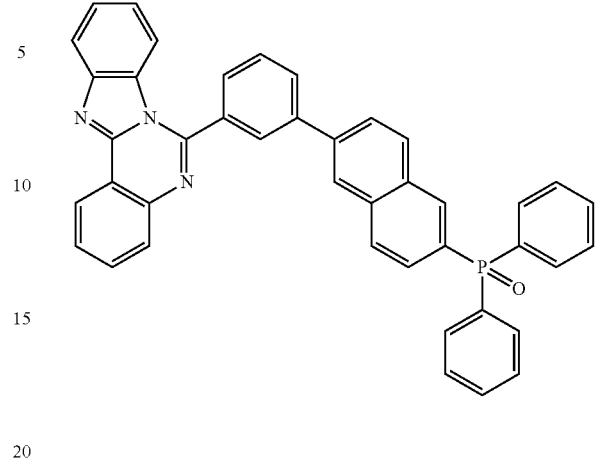
[Formula 1-5]
[Formula 1-7]
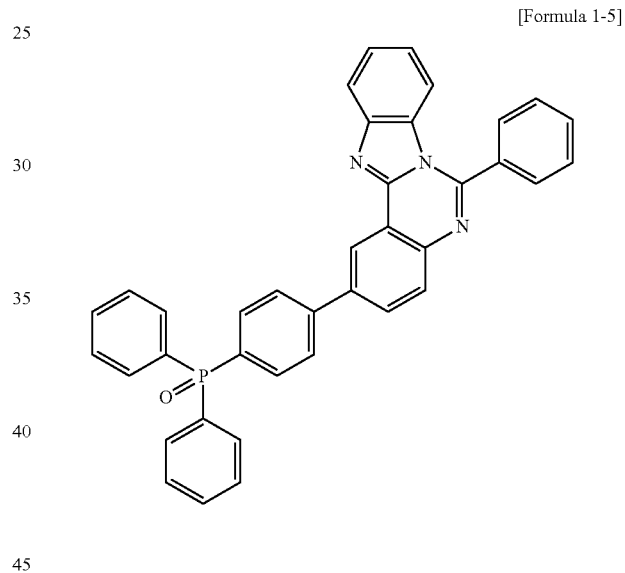
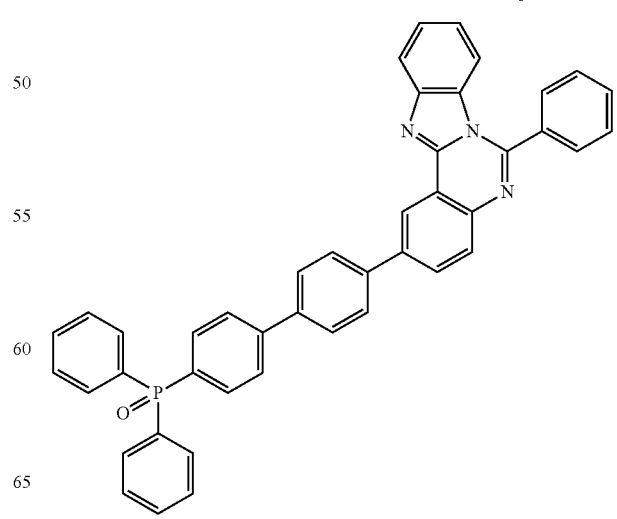

[Formula 1-8]
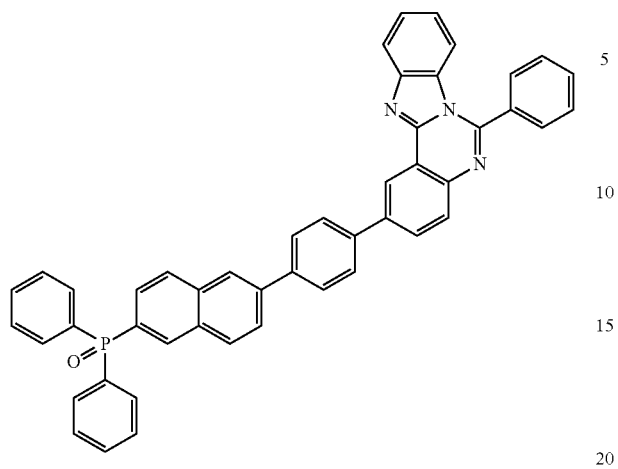
[Formula 1-9]
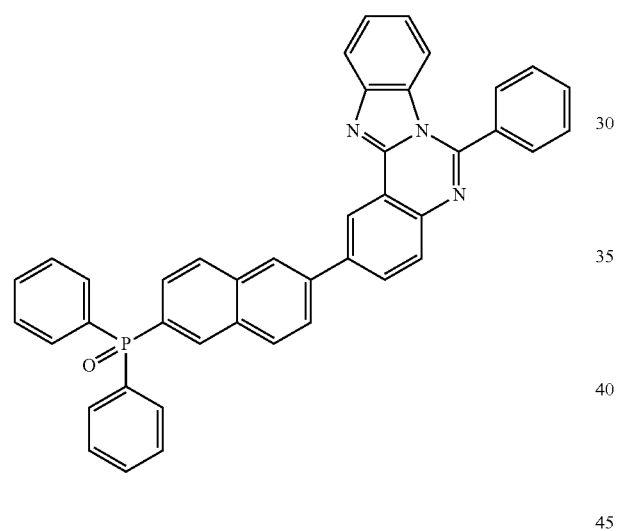
[Formula 1-10]
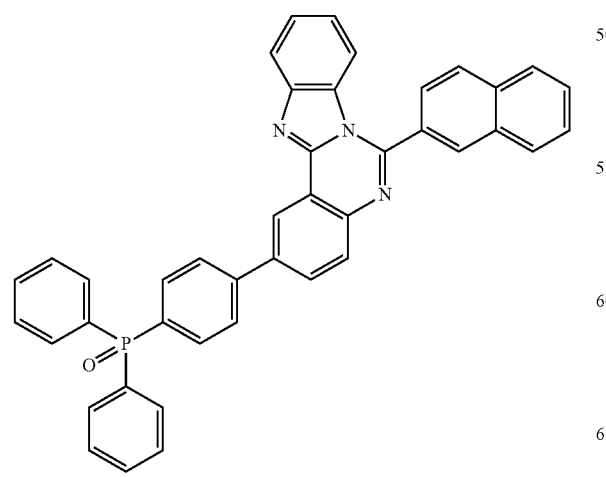
[Formula 1-11]
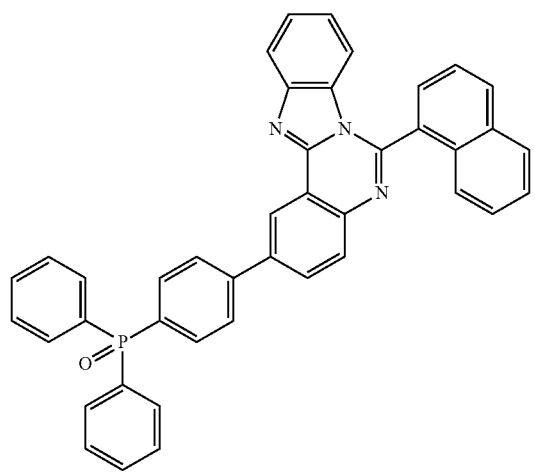
[Formula 1-12]
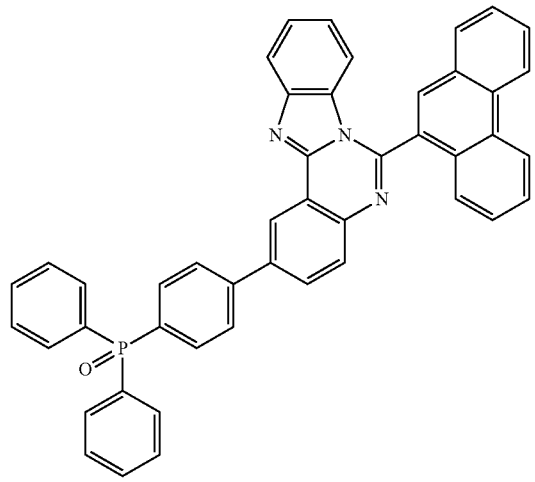
[Formula 1-13]
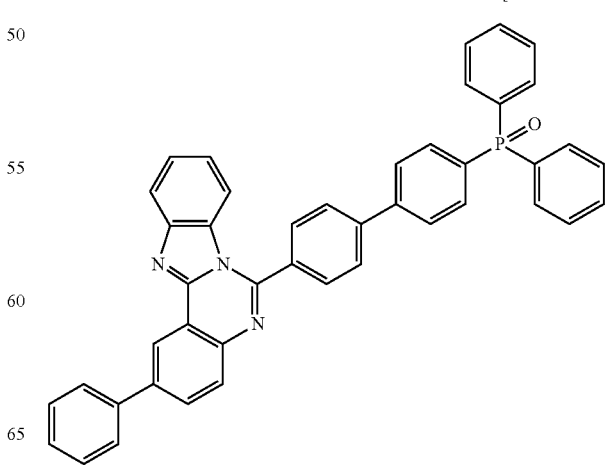

[Formula 1-14]
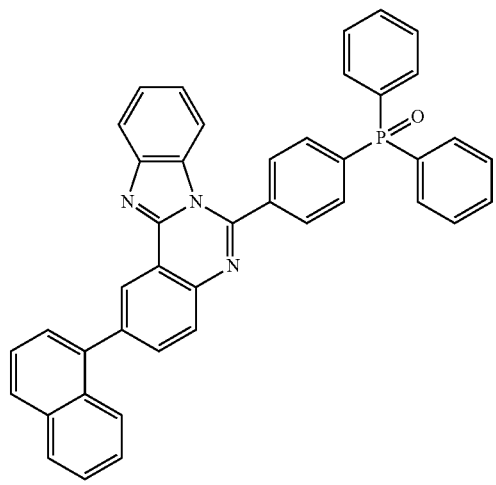
[Formula 1-15]
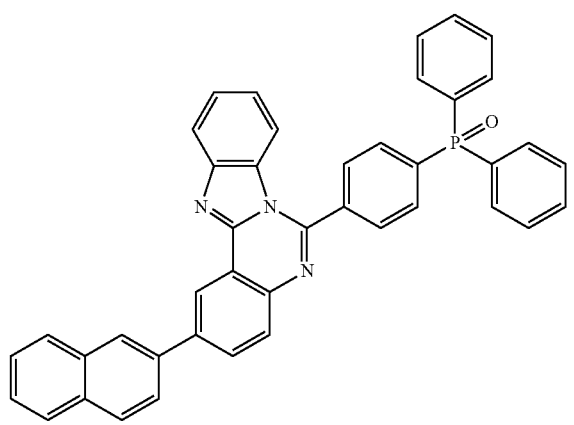
[Formula 1-17]
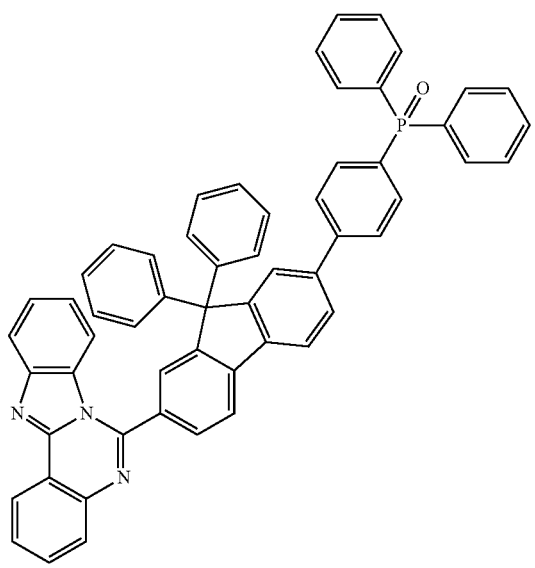
[Formula 1-18]
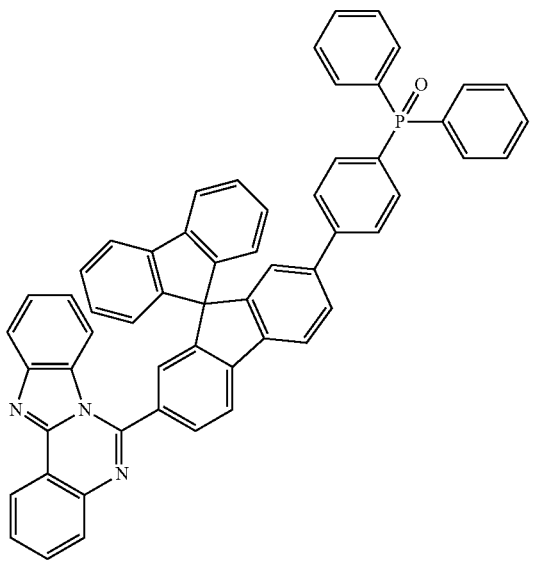
[Formula 1-19]
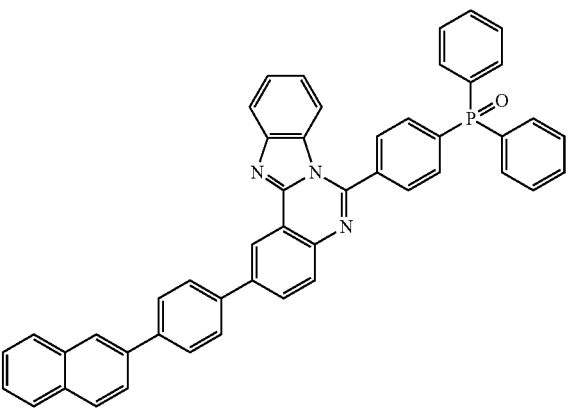
[Formula 1-20]
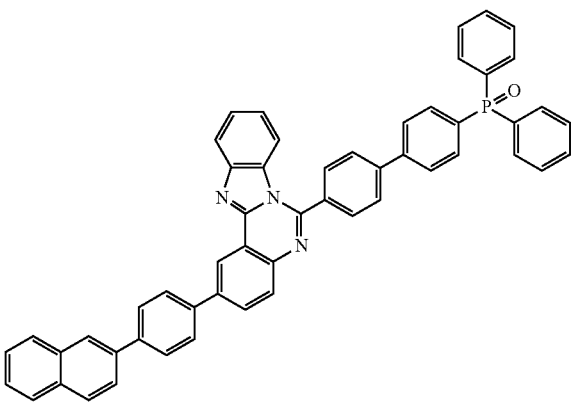

[Formula 1-22]

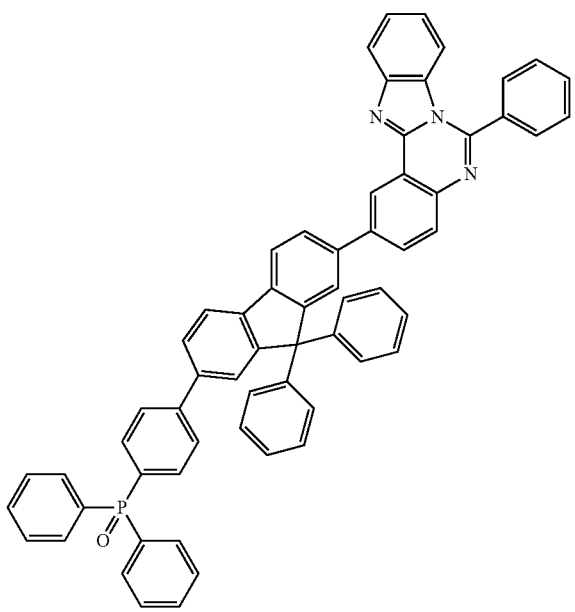

[Formula 1-23]

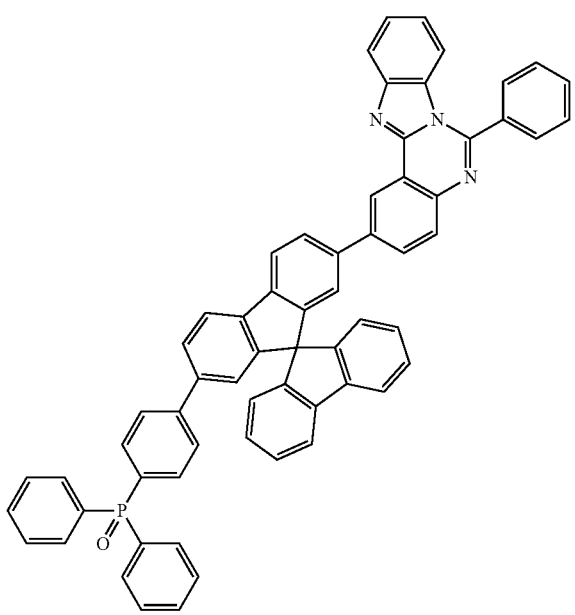

[Formula 1-24]

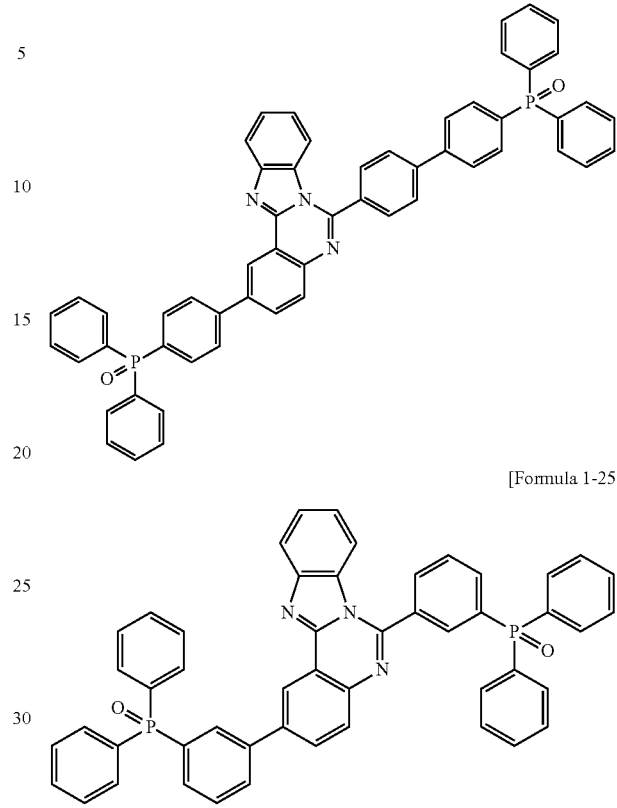

[Formula 1-25]

[Formula 1-26]

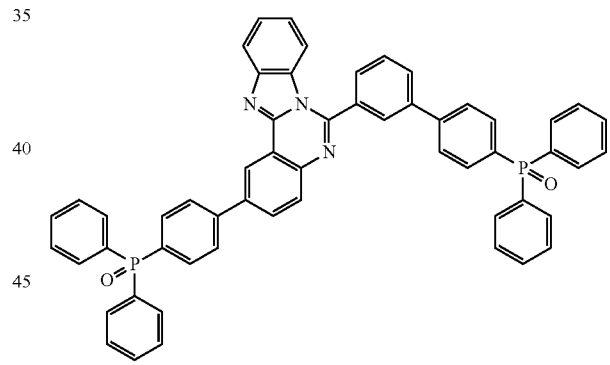

4. An organic electronic device, comprising:
a first electrode;
a second electrode;
and one or more organic material layers disposed between the first electrode and the second electrode,
wherein one or more layers of the organic material layers comprise the compound represented by Formula 1 claim 1.

5. The organic electron device of claim 4, wherein the organic material layer comprises one or more layers of a hole injection layer, a hole transporting layer, and a layer which injects and transports holes simultaneously, and one or more layers of the layers comprise the compound represented by Formula 1.

6. The organic electronic device of claim 4, wherein the organic material layer comprises a light emitting layer, and the light emitting layer comprises the compound represented by Formula 1.

7. The organic electron device of claim 4, wherein the organic material layer comprises one or more layers of an electron transporting layer, an electron injection layer, and a layer which transports and injects electrons simultaneously, and one or more layers of the layers comprise the compound represented by Formula 1.

8. The organic electronic device of claim 4, wherein the organic electronic device is selected from the group consisting of an organic light emitting device, an organic phosphorescence device, an organic solar cell, an organic photoconductor (OPC) and an organic transistor.

* * * * *

UNITED STATES PATENT AND TRADEMARK OFFICE
CERTIFICATE OF CORRECTION

PATENT NO. : 8,999,530 B2
APPLICATION NO. : 14/125552
DATED : April 7, 2015
INVENTOR(S) : Changhwan Shin et al.

Page 1 of 1

It is certified that error appears in the above-identified patent and that said Letters Patent is hereby corrected as shown below:

IN THE CLAIMS:

At column 36, line 47:

Please delete "wherein."

At column 36, line 48:

Please replace "R5 to R8" with "R5 and R8."

Signed and Sealed this
Eleventh Day of August, 2015

Michelle K. Lee
*Director of the United States Patent and Trademark Office*